US010595896B2

(12) United States Patent
Miller

(10) Patent No.: US 10,595,896 B2
(45) Date of Patent: Mar. 24, 2020

(54) APPARATUS FOR ACCESSING BONE MARROW INCLUDING DEPTH CONTROL MECHANISM

(71) Applicant: TELEFLEX MEDICAL DEVICES S.À R.L., Luxembourg OT (LU)

(72) Inventor: Larry Miller, Spring Branch, TX (US)

(73) Assignee: TELEFLEX LIFE SCIENCES LIMITED, Valletta, MT (US)

( * ) Notice: Subject to any disclaimer, the term of this patent is extended or adjusted under 35 U.S.C. 154(b) by 497 days.

(21) Appl. No.: 15/084,541

(22) Filed: Mar. 30, 2016

(65) Prior Publication Data

US 2016/0206346 A1    Jul. 21, 2016

Related U.S. Application Data

(63) Continuation of application No. 11/023,173, filed on Dec. 27, 2004, now Pat. No. 9,314,228, which is a (Continued)

(30) Foreign Application Priority Data

Nov. 11, 2004    (TW) .............................. 93134480 A

(51) Int. Cl.
*A61B 17/34* (2006.01)
*A61B 10/02* (2006.01)
(Continued)

(52) U.S. Cl.
CPC ............ *A61B 17/34* (2013.01); *A61B 10/025* (2013.01); *A61B 17/32002* (2013.01);
(Continued)

(58) Field of Classification Search
CPC ............ A61B 17/3403; A61B 17/3415; A61B 17/3472; A61B 10/0045; A61B 10/0233
(Continued)

(56) References Cited

U.S. PATENT DOCUMENTS 1,539,637 A   5/1925   Bronner
2,317,648 A   4/1943   Siqveland
(Continued)

FOREIGN PATENT DOCUMENTS

CA    2138842      6/1996
CA    2 454 600    2/2003
(Continued)

OTHER PUBLICATIONS

"Proven reliability for quality bone marrow samples", Special Procedures, Cardinal Health, 6 pages, 2003.
(Continued)

*Primary Examiner* — Anu Ramana
(74) *Attorney, Agent, or Firm* — Baker & Hostetler LLP

(57) ABSTRACT

An apparatus for accessing bone marrow inside a bone is provided. The apparatus may include a penetrator assembly having a tissue penetrator and a hub. The tissue penetrator my have a hollow cannula disposed in fixed relation to the hub. The apparatus may also have a driver configured to insert a portion of the tissue penetrator into the bone and bone marrow, and a depth control mechanism configured to control the depth of penetration of the tissue penetrator into the bone and bone marrow. The depth control mechanism may have a sensor configured to detect a position of the bone and bone marrow. The depth control mechanism may also have a mechanical stop.

18 Claims, 10 Drawing Sheets

Related U.S. Application Data continuation of application No. 10/987,051, filed on Nov. 12, 2004, now Pat. No. 8,142,365, which is a continuation-in-part of application No. 10/449,503, filed on May 30, 2003, now Pat. No. 7,670,328.

(60) Provisional application No. 60/519,462, filed on Nov. 12, 2003, provisional application No. 60/384,756, filed on May 31, 2002.

(51) Int. Cl.
| | |
|---|---|
| *A61B 17/32* | (2006.01) |
| *A61B 17/3205* | (2006.01) |
| *A61M 5/158* | (2006.01) |
| *A61M 5/46* | (2006.01) |
| *A61B 17/16* | (2006.01) |
| *A61B 17/00* | (2006.01) |
| *A61B 90/11* | (2016.01) |
| *A61B 90/70* | (2016.01) |
| *A61B 90/00* | (2016.01) |
| *A61B 34/30* | (2016.01) |
| *A61B 90/25* | (2016.01) |

(52) U.S. Cl.
CPC .... *A61B 17/32053* (2013.01); *A61B 17/3403* (2013.01); *A61B 17/3472* (2013.01); *A61B 17/3476* (2013.01); *A61M 5/158* (2013.01); *A61M 5/46* (2013.01); *A61B 10/0283* (2013.01); *A61B 17/1637* (2013.01); *A61B 17/1691* (2013.01); *A61B 34/30* (2016.02); *A61B 90/11* (2016.02); *A61B 90/25* (2016.02); *A61B 90/70* (2016.02); *A61B 2010/0258* (2013.01); *A61B 2017/0046* (2013.01); *A61B 2017/00398* (2013.01); *A61B 2017/00734* (2013.01); *A61B 2090/036* (2016.02); *A61B 2090/0813* (2016.02); *A61B 2217/005* (2013.01); *A61M 2005/1581* (2013.01); *A61M 2005/1585* (2013.01)

(58) Field of Classification Search
USPC ........ 606/167–172; 600/562, 564, 566, 567; 604/93.01, 117
See application file for complete search history.

(56) References Cited

U.S. PATENT DOCUMENTS

| | | | |
|---|---|---|---|
| 2,419,045 A | 4/1947 | Whittaker | |
| 2,773,501 A | 12/1956 | Young | |
| 3,104,448 A | 9/1963 | Morrow et al. | |
| 3,120,845 A | 2/1964 | Horner | |
| 3,173,417 A | 3/1965 | Horner | |
| 3,175,554 A | 3/1965 | Stewart | |
| 3,507,276 A | 4/1970 | Burgess et al. | |
| 3,543,966 A | 12/1970 | Ryan et al. | |
| 3,697,223 A | 10/1972 | Kovalcik et al. | |
| 3,802,555 A | 4/1974 | Grasty et al. | |
| 3,815,605 A | 6/1974 | Schmidt et al. | |
| 3,835,860 A | 9/1974 | Garretson et al. | |
| 3,893,445 A | 7/1975 | Hofsess | |
| 3,991,765 A | 11/1976 | Cohen | |
| 4,021,920 A | 5/1977 | Kirschner et al. | |
| 4,099,518 A | 7/1978 | Baylis et al. | |
| 4,124,026 A | 11/1978 | Berner et al. | |
| 4,142,517 A | 3/1979 | Stravropoulos et al. | |
| 4,170,993 A | 10/1979 | Alvarez | |
| 4,185,619 A | 1/1980 | Reiss | |
| 4,194,505 A | 3/1980 | Schmitz | |
| 4,258,722 A | 3/1981 | Sessions et al. | |
| 4,262,676 A | 4/1981 | Jamshidi | |
| 4,306,570 A | 12/1981 | Matthews | |
| 4,316,463 A | 2/1982 | Schmitz et al. | |
| 4,333,459 A | 6/1982 | Becker | |
| 4,381,777 A | 5/1983 | Garnier | |
| 4,420,085 A | 12/1983 | Wilson et al. | |
| 4,441,563 A | 4/1984 | Walton, II | |
| 4,469,109 A | 9/1984 | Mehl | |
| 4,484,577 A | 11/1984 | Sackner et al. | |
| 4,543,966 A | 10/1985 | Islam et al. | |
| 4,553,539 A | 11/1985 | Morris | |
| 4,605,011 A | 8/1986 | Naslund | |
| 4,620,539 A | 11/1986 | Andrews et al. | |
| 4,630,616 A | 12/1986 | Tretinyak | |
| 4,646,731 A | 3/1987 | Brower | |
| 4,654,492 A | 3/1987 | Koerner et al. | |
| 4,655,226 A | 4/1987 | Lee | |
| 4,659,329 A | 4/1987 | Annis | |
| 4,692,073 A | 9/1987 | Martindell | |
| 4,711,636 A | 12/1987 | Bierman | |
| 4,713,061 A | 12/1987 | Tarello et al. | |
| 4,716,901 A | 1/1988 | Jackson et al. | |
| 4,723,945 A | 2/1988 | Theiling | |
| 4,736,850 A | 4/1988 | Bowman et al. | |
| 4,758,225 A | 7/1988 | Cox et al. | |
| 4,762,118 A | 8/1988 | Lia et al. | |
| 4,772,261 A | 9/1988 | Von Hoff et al. | |
| 4,787,893 A | 11/1988 | Villette | |
| 4,793,363 A | 12/1988 | Ausherman et al. | |
| 4,867,158 A | 9/1989 | Sugg | |
| 4,919,146 A | 4/1990 | Rhinehart et al. | |
| 4,921,013 A | 5/1990 | Spalink et al. | |
| 4,935,010 A | 6/1990 | Cox et al. | |
| 4,940,459 A | 7/1990 | Noce | |
| 4,944,677 A | 7/1990 | Alexandre | |
| 4,969,870 A | 11/1990 | Kramer et al. | |
| 4,986,279 A | 1/1991 | O'Neill | |
| 5,002,546 A | 3/1991 | Romano | |
| 5,025,797 A | 6/1991 | Baran | |
| 5,036,860 A | 8/1991 | Leigh et al. | |
| 5,057,085 A | 10/1991 | Kopans | |
| 5,074,311 A | 12/1991 | Hasson | |
| 5,116,324 A | 5/1992 | Brierley et al. | |
| 5,120,312 A | 6/1992 | Wigness et al. | |
| 5,122,114 A | 6/1992 | Miller et al. | |
| 5,133,359 A | 7/1992 | Kedem | |
| 5,137,518 A | 8/1992 | Mersch | |
| 5,139,500 A | 8/1992 | Schwartz | |
| RE34,056 E | 9/1992 | Lindgren et al. | |
| 5,172,701 A | 12/1992 | Leigh | |
| 5,172,702 A | 12/1992 | Leigh et al. | |
| 5,176,643 A | 1/1993 | Kramer et al. | |
| 5,183,054 A * | 2/1993 | Burkholder | A61B 10/0275 600/564 |
| 5,195,985 A | 3/1993 | Hall | |
| 5,203,056 A | 4/1993 | Funk et al. | |
| 5,207,697 A | 5/1993 | Carusillo et al. | |
| 5,249,583 A | 10/1993 | Mallaby | |
| 5,257,632 A | 11/1993 | Turkel et al. | |
| 5,261,877 A | 11/1993 | Fine et al. | |
| 5,269,785 A | 12/1993 | Bonutti | |
| 5,279,306 A | 1/1994 | Mehl | |
| 5,312,364 A | 5/1994 | Jacobs | |
| 5,324,300 A | 6/1994 | Elias et al. | |
| 5,332,398 A | 7/1994 | Miller et al. | |
| 5,333,790 A | 8/1994 | Christopher | |
| 5,341,823 A | 8/1994 | Manosalva et al. | |
| 5,348,022 A | 9/1994 | Leigh et al. | |
| 5,357,974 A | 10/1994 | Baldridge | |
| 5,368,046 A | 11/1994 | Scarfone et al. | |
| 5,372,583 A | 12/1994 | Roberts et al. | |
| 5,383,859 A | 1/1995 | Sewell, Jr. | |
| 5,385,553 A | 1/1995 | Hart et al. | |
| 5,400,798 A | 3/1995 | Baran | |
| 5,405,348 A | 4/1995 | Anspach et al. | |
| 5,423,824 A | 6/1995 | Akerfeldt et al. | |
| 5,431,655 A | 7/1995 | Melker et al. | |
| 5,451,210 A | 9/1995 | Kramer et al. | |
| 5,484,442 A | 1/1996 | Melker et al. | |
| D369,858 S | 5/1996 | Baker et al. | |
| 5,526,821 A | 6/1996 | Jamshidi | |

(56) References Cited

U.S. PATENT DOCUMENTS

| | | |
|---|---|---|
| 5,529,580 A | 6/1996 | Kusunoki et al. |
| 5,549,565 A | 8/1996 | Ryan et al. |
| 5,554,154 A | 9/1996 | Rosenberg |
| 5,556,399 A | 9/1996 | Huebner |
| 5,558,737 A | 9/1996 | Brown et al. |
| 5,571,133 A | 11/1996 | Yoon |
| 5,586,847 A | 12/1996 | Mattern, Jr. et al. |
| 5,591,188 A | 1/1997 | Waisman |
| 5,595,186 A | 1/1997 | Rubinstein et al. |
| 5,601,559 A | 2/1997 | Melker et al. |
| 5,632,747 A | 5/1997 | Scarborough et al. |
| 5,672,155 A | 9/1997 | Riley et al. |
| 5,713,368 A | 2/1998 | Leigh |
| 5,724,873 A | 3/1998 | Hillinger |
| 5,733,262 A | 3/1998 | Paul |
| 5,752,923 A | 5/1998 | Terwilliger |
| 5,762,639 A | 6/1998 | Gibbs |
| 5,766,221 A | 6/1998 | Benderev et al. |
| 5,769,086 A | 6/1998 | Ritchart et al. |
| 5,779,708 A | 7/1998 | Wu |
| 5,800,389 A | 9/1998 | Burney et al. |
| 5,807,277 A | 9/1998 | Swaim |
| 5,810,826 A | 9/1998 | Akerfeldt et al. |
| 5,817,052 A | 10/1998 | Johnson et al. |
| 5,823,970 A | 10/1998 | Terwilliger |
| D403,405 S | 12/1998 | Terwilliger |
| 5,858,005 A | 1/1999 | Kriesel |
| 5,868,711 A | 2/1999 | Kramer et al. |
| 5,868,750 A | 2/1999 | Schultz |
| 5,873,510 A | 2/1999 | Hirai et al. |
| 5,885,226 A | 3/1999 | Rubinstein et al. |
| 5,891,085 A | 4/1999 | Lilley et al. |
| 5,911,701 A | 6/1999 | Miller et al. |
| 5,911,708 A | 6/1999 | Teirstein |
| 5,916,229 A | 6/1999 | Evans |
| 5,919,172 A | 7/1999 | Golba, Jr. |
| 5,924,864 A | 7/1999 | Loge et al. |
| 5,927,976 A | 7/1999 | Wu |
| 5,928,238 A | 7/1999 | Scarborough et al. |
| 5,941,706 A | 8/1999 | Ura |
| 5,941,851 A | 8/1999 | Coffey et al. |
| 5,960,797 A | 10/1999 | Kramer et al. |
| 5,980,545 A | 11/1999 | Pacala et al. |
| 5,993,417 A | 11/1999 | Yerfino et al. |
| 5,993,454 A | 11/1999 | Longo |
| 6,007,496 A | 12/1999 | Brannon |
| 6,017,348 A | 1/2000 | Hart et al. |
| 6,018,094 A | 1/2000 | Fox |
| 6,022,324 A | 2/2000 | Skinner |
| 6,027,458 A | 2/2000 | Janssens |
| 6,033,369 A | 3/2000 | Goldenberg |
| 6,033,411 A | 3/2000 | Preissman |
| 6,063,037 A | 5/2000 | Mittermeier et al. |
| 6,071,284 A | 6/2000 | Fox |
| 6,080,115 A | 6/2000 | Rubinstein et al. |
| 6,083,176 A | 7/2000 | Terwilliger |
| 6,086,544 A | 7/2000 | Hibner et al. |
| 6,096,042 A | 8/2000 | Herbert |
| 6,102,887 A | 8/2000 | Altman |
| 6,102,915 A | 8/2000 | Bresler et al. |
| 6,106,484 A | 8/2000 | Terwilliger |
| 6,110,128 A | 8/2000 | Andelin et al. |
| 6,110,129 A | 8/2000 | Terwilliger |
| 6,110,174 A | 8/2000 | Nichter |
| 6,120,462 A | 9/2000 | Hibner et al. |
| 6,135,769 A | 10/2000 | Kwan |
| 6,152,918 A | 11/2000 | Padilla et al. |
| 6,159,163 A | 12/2000 | Strauss et al. |
| 6,162,203 A | 12/2000 | Haaga |
| 6,171,276 B1 * | 1/2001 | Lippe ................... A61M 5/20 128/DIG. 1 |
| 6,183,442 B1 | 2/2001 | Athanasiou et al. |
| 6,210,376 B1 | 4/2001 | Grayson |
| 6,217,561 B1 | 4/2001 | Gibbs |
| 6,221,029 B1 | 4/2001 | Mathis et al. |
| 6,228,049 B1 | 5/2001 | Schroeder et al. |
| 6,228,088 B1 | 5/2001 | Miller et al. |
| 6,238,355 B1 | 5/2001 | Daum |
| 6,247,928 B1 | 6/2001 | Meller et al. |
| 6,248,110 B1 | 6/2001 | Reiley et al. |
| 6,257,351 B1 | 7/2001 | Ark et al. |
| 6,267,763 B1 | 7/2001 | Castro |
| 6,273,715 B1 | 8/2001 | Meller et al. |
| 6,273,862 B1 | 8/2001 | Privitera et al. |
| 6,283,925 B1 | 9/2001 | Terwilliger |
| 6,283,970 B1 | 9/2001 | Lubinus |
| 6,287,114 B1 | 9/2001 | Meller et al. |
| 6,302,852 B1 | 10/2001 | Fleming, III et al. |
| 6,309,358 B1 | 10/2001 | Okubo |
| 6,312,394 B1 | 11/2001 | Fleming, III |
| 6,315,737 B1 | 11/2001 | Skinner |
| 6,325,806 B1 | 12/2001 | Fox |
| 6,328,701 B1 | 12/2001 | Terwilliger |
| 6,328,744 B1 | 12/2001 | Harari et al. |
| 6,358,252 B1 | 3/2002 | Shapira |
| 6,402,701 B1 | 6/2002 | Kaplan et al. |
| 6,419,490 B1 | 7/2002 | Kitchings Weathers, Jr. |
| 6,425,888 B1 | 7/2002 | Embleton et al. |
| 6,428,487 B1 | 8/2002 | Burdorff et al. |
| 6,443,910 B1 | 9/2002 | Krueger et al. |
| 6,458,117 B1 | 10/2002 | Pollins |
| 6,468,248 B1 | 10/2002 | Gibbs |
| 6,478,751 B1 | 11/2002 | Krueger et al. |
| 6,488,636 B2 | 12/2002 | Bryan et al. |
| 6,523,698 B1 | 2/2003 | Dennehey et al. |
| 6,527,736 B1 | 3/2003 | Attinger et al. |
| 6,527,778 B2 | 3/2003 | Athanasiou et al. |
| 6,540,694 B1 | 4/2003 | Van Bladel et al. |
| 6,547,511 B1 | 4/2003 | Adams |
| 6,547,561 B2 | 4/2003 | Meller et al. |
| 6,547,755 B1 * | 4/2003 | Lippe ................... A61M 5/20 604/154 |
| 6,554,779 B2 | 4/2003 | Viola et al. |
| 6,555,212 B2 | 4/2003 | Boiocchi et al. |
| 6,575,745 B2 | 6/2003 | Meller et al. |
| 6,575,919 B1 | 6/2003 | Reiley et al. |
| 6,582,399 B1 | 6/2003 | Smith et al. |
| 6,585,622 B1 | 7/2003 | Shum et al. |
| 6,595,911 B2 | 7/2003 | LoVuolo |
| 6,595,979 B1 | 7/2003 | Epstein et al. |
| 6,613,054 B2 | 9/2003 | Scribner et al. |
| 6,616,632 B2 | 9/2003 | Sharp et al. |
| 6,620,111 B2 | 9/2003 | Stehens et al. |
| 6,626,848 B2 | 9/2003 | Nueenfeldt |
| 6,626,887 B1 | 9/2003 | Wu |
| 6,638,235 B2 | 10/2003 | Miller et al. |
| 6,641,395 B2 | 11/2003 | Kumar et al. |
| 6,656,133 B2 | 12/2003 | Voegele et al. |
| 6,689,072 B2 | 2/2004 | Kaplan et al. |
| 6,702,760 B2 | 3/2004 | Krause et al. |
| 6,702,761 B1 | 3/2004 | Damadian et al. |
| 6,706,016 B2 | 3/2004 | Cory et al. |
| 6,716,192 B1 | 4/2004 | Orosz, Jr. |
| 6,716,215 B1 | 4/2004 | David et al. |
| 6,716,216 B1 | 4/2004 | Boucher et al. |
| 6,726,649 B2 | 4/2004 | Swenson et al. |
| 6,730,043 B2 | 5/2004 | Krueger et al. |
| 6,730,044 B2 | 5/2004 | Stephens et al. |
| 6,749,576 B2 | 6/2004 | Bauer |
| 6,752,768 B2 | 6/2004 | Burdoff et al. |
| 6,752,816 B2 | 6/2004 | Culp et al. |
| 6,758,824 B1 | 7/2004 | Miller et al. |
| 6,761,726 B1 | 7/2004 | Findlay et al. |
| 6,796,957 B2 | 9/2004 | Carpenter et al. |
| 6,846,314 B2 | 1/2005 | Shapira |
| 6,849,051 B2 | 2/2005 | Sramek et al. |
| 6,855,148 B2 | 2/2005 | Foley et al. |
| 6,860,860 B2 | 3/2005 | Viola |
| 6,875,183 B2 | 4/2005 | Cervi |
| 6,875,219 B2 | 4/2005 | Arramon et al. |
| 6,884,245 B2 | 4/2005 | Spranza |
| 6,887,209 B2 | 5/2005 | Kadziauskas et al. |
| 6,890,308 B2 | 5/2005 | Islam |
| 6,905,486 B2 | 6/2005 | Gibbs |

(56) References Cited

U.S. PATENT DOCUMENTS

| | | |
|---|---|---|
| 6,930,461 B2 | 8/2005 | Ruthowski |
| 6,942,669 B2 | 9/2005 | Kurc |
| 6,969,373 B2 | 11/2005 | Schwartz et al. |
| 7,008,381 B2 | 3/2006 | Janssens |
| 7,008,383 B1 | 3/2006 | Damadian et al. |
| 7,008,394 B2 | 3/2006 | Geise et al. |
| 7,025,732 B2 | 4/2006 | Thompson et al. |
| 7,063,672 B2 | 6/2006 | Schramm |
| 7,081,123 B2 | 7/2006 | Merboth et al. |
| 7,137,985 B2 | 11/2006 | Jahng |
| 7,169,127 B2 | 1/2007 | Epstein et al. |
| 7,207,949 B2 | 4/2007 | Miles et al. |
| 7,226,450 B2 | 6/2007 | Athanasiou et al. |
| 7,229,401 B2 | 6/2007 | Kindlein |
| 7,736,322 B2 | 6/2010 | Roe et al. |
| 2001/0014439 A1 | 8/2001 | Meller et al. |
| 2001/0047183 A1 | 11/2001 | Privitera et al. |
| 2001/0053888 A1 | 12/2001 | Athanasiou et al. |
| 2002/0042581 A1 | 4/2002 | Cervi |
| 2002/0055713 A1 | 5/2002 | Gibbs |
| 2002/0120212 A1 | 8/2002 | Ritchart et al. |
| 2002/0138021 A1 | 9/2002 | Pflueger |
| 2002/0143269 A1 | 10/2002 | Neuenfeldt |
| 2002/0151821 A1 | 10/2002 | Castellacci |
| 2003/0028146 A1 | 2/2003 | Aves |
| 2003/0032939 A1 | 2/2003 | Gibbs |
| 2003/0036747 A1 | 2/2003 | Ie et al. |
| 2003/0050574 A1 | 3/2003 | Krueger |
| 2003/0078586 A1 | 4/2003 | Shapira |
| 2003/0114858 A1 | 6/2003 | Athanasiou et al. |
| 2003/0125639 A1 | 7/2003 | Fisher et al. |
| 2003/0153842 A1 | 8/2003 | Lamoureux et al. |
| 2003/0191414 A1 | 10/2003 | Reiley et al. |
| 2003/0195436 A1 | 10/2003 | Van Bladel et al. |
| 2003/0195524 A1 | 10/2003 | Barner |
| 2003/0199787 A1 | 10/2003 | Schwindt |
| 2003/0216667 A1 | 11/2003 | Viola |
| 2003/0225344 A1 | 12/2003 | Miller |
| 2003/0225364 A1 | 12/2003 | Kraft et al. |
| 2003/0225411 A1 | 12/2003 | Miller |
| 2004/0010236 A1 | 1/2004 | Morawski et al. |
| 2004/0019297 A1 | 1/2004 | Angel |
| 2004/0019299 A1 | 1/2004 | Richart et al. |
| 2004/0034280 A1 | 2/2004 | Privitera et al. |
| 2004/0049128 A1 | 3/2004 | Miller et al. |
| 2004/0064136 A1 | 4/2004 | Papineau et al. |
| 2004/0073139 A1 | 4/2004 | Hirsch et al. |
| 2004/0092946 A1 | 5/2004 | Bagga et al. |
| 2004/0153003 A1 | 8/2004 | Cicenas et al. |
| 2004/0158172 A1 | 8/2004 | Hancock |
| 2004/0158173 A1 | 8/2004 | Voegele et al. |
| 2004/0162505 A1 | 8/2004 | Kaplan et al. |
| 2004/0191897 A1 | 9/2004 | Muschler |
| 2004/0210161 A1 | 10/2004 | Burdorff et al. |
| 2004/0215102 A1 | 10/2004 | Ikehara et al. |
| 2004/0220497 A1 | 11/2004 | Findlay et al. |
| 2005/0027210 A1 | 2/2005 | Miller |
| 2005/0040060 A1 | 2/2005 | Anderson et al. |
| 2005/0075581 A1 | 4/2005 | Schwindt |
| 2005/0085838 A1 | 4/2005 | Thompson et al. |
| 2005/0101880 A1 | 5/2005 | Cicenas et al. |
| 2005/0113716 A1 | 5/2005 | Mueller, Jr. et al. |
| 2005/0124915 A1 | 6/2005 | Eggers et al. |
| 2005/0131345 A1 | 6/2005 | Miller |
| 2005/0148940 A1 | 7/2005 | Miller |
| 2005/0165328 A1 | 7/2005 | Heske et al. |
| 2005/0165403 A1 | 7/2005 | Miller |
| 2005/0165404 A1 | 7/2005 | Miller |
| 2005/0171504 A1 | 8/2005 | Miller |
| 2005/0182394 A1 | 8/2005 | Spero et al. |
| 2005/0200087 A1 | 9/2005 | Vasudeva et al. |
| 2005/0203439 A1 | 9/2005 | Heske et al. |
| 2005/0209530 A1 | 9/2005 | Pflueger |
| 2005/0215921 A1 | 9/2005 | Hibner et al. |
| 2005/0228309 A1 | 10/2005 | Fisher et al. |
| 2005/0261693 A1 | 11/2005 | Miller et al. |
| 2006/0011506 A1 | 1/2006 | Riley |
| 2006/0015066 A1 | 1/2006 | Turieo et al. |
| 2006/0036212 A1 | 2/2006 | Miller |
| 2006/0052790 A1 | 3/2006 | Miller |
| 2006/0074345 A1 | 4/2006 | Hibner |
| 2006/0079774 A1 | 4/2006 | Anderson |
| 2006/0089565 A1 | 4/2006 | Schramm |
| 2006/0122535 A1 | 6/2006 | Daum |
| 2006/0129082 A1 | 6/2006 | Rozga |
| 2006/0144548 A1 | 7/2006 | Beckman et al. |
| 2006/0149163 A1 | 7/2006 | Hibner et al. |
| 2006/0167377 A1 | 7/2006 | Richart et al. |
| 2006/0167378 A1 | 7/2006 | Miller |
| 2006/0167379 A1 | 7/2006 | Miller |
| 2006/0184063 A1 | 8/2006 | Miller |
| 2006/0189940 A1 | 8/2006 | Kirsch |
| 2007/0016100 A1 | 1/2007 | Miller |
| 2007/0049945 A1 | 3/2007 | Miller |
| 2007/0149920 A1 | 6/2007 | Michels et al. |
| 2007/0213735 A1 | 9/2007 | Sandat et al. |
| 2007/0270775 A1 | 11/2007 | Miller et al. |
| 2008/0015467 A1 | 1/2008 | Miller |
| 2008/0015468 A1 | 1/2008 | Miller |
| 2008/0045857 A1 | 2/2008 | Miller |
| 2008/0045860 A1 | 2/2008 | Miller et al. |
| 2008/0045861 A1 | 2/2008 | Miller et al. |
| 2008/0045965 A1 | 2/2008 | Miller et al. |
| 2008/0140014 A1 | 6/2008 | Miller et al. |
| 2008/0215056 A1 | 9/2008 | Miller et al. |
| 2008/0221580 A1 | 9/2008 | Miller et al. |
| 2011/0186456 A1 | 8/2011 | Bertazzoni et al. |

FOREIGN PATENT DOCUMENTS

| | | |
|---|---|---|
| EP | 517000 | 12/1992 |
| EP | 0807412 | 11/1997 |
| EP | 1314452 | 5/2003 |
| FR | 853349 | 3/1940 |
| FR | 2457105 | 12/1980 |
| FR | 2516386 | 5/1983 |
| GB | 2130890 | 6/1984 |
| WO | 93/07819 | 4/1993 |
| WO | 96/31164 | 10/1996 |
| WO | 98/06337 | 2/1998 |
| WO | 99/18866 | 4/1999 |
| WO | 99/52444 | 10/1999 |
| WO | 00/56220 | 9/2000 |
| WO | 02/41792 | 5/2002 |
| WO | 02/096497 | 12/2002 |
| WO | 2005/110259 | 11/2005 |
| WO | 2005/112800 | 12/2005 |
| WO | 2008/081438 | 7/2008 |

OTHER PUBLICATIONS

F.A.S.T. 1 Intraosseous Infusion System with Depth-Control Mechanism Brochure, 6 pages, 2000.

Richard O. Cummings et al., "ACLS—Principles and Practice", ACLS—The Reference Textbook, American Heart Association, pp. 214-218, 2003.

Riley et al., "A Pathologist's Perspective on Bone Marrow Aspiration Biopsy: I. Performing a Bone Marrow Examination," Journal of Clinical Laboratory Analysis 18, pp. 70-90, 2004.

Astrom, K.G., "Automatic Biopsy Instruments Used Through a Coaxial Bone Biopsy System with an Eccentric Drill Tip," Acta Radiologica, 1995; 36:237-242, May 1995.

Astrom, K. Gunnar O., "CT-guided Transsternal Core Biopsy of Anterior Mediastinal Masses," Radiology 1996; 199:564-567, May 1996.

Pediatrics, Official Journal of the American Academy of Pediatrics, Pediatrics, 2005 American Heart Association Guidelines for Cardiopulmonary Resuscitation and Emergency Cardiovascular Care of Pediatric and Neonatal Patients:Pediatric Advanced Life Support, Downloaded from www.pediatrics.org, Feb. 21, 2007.

Liakat A. Parapia, Trepanning or trephines: a history of bone marrow biopsy, British Journal of Haematology, pp. 14-19, 2007.

(56) References Cited

OTHER PUBLICATIONS

Pediatric Emergency, Intraosseous Infusion for Administration of Fluids and Drugs, www.cookgroup.com, 1 pg, 2000.
Michael Trotty, "Technology (A Special Report)—The Wall Street Journal 2008 Technology Innovation Awards—This years winners include: an IV alternative, a better way to make solar panels, a cheap, fuel efficient car and a better way to see in the dark", The Wall Street Journal, Factiva, 5 pages, 2008.
Buckley et al., CT-guided bone biopsy: Initial experience with commercially available hand held Black and Decker drill, European Journal of Radiology 61, pp. 176-180, 2007.
Hakan et al., CT-guided Bone BiopsyPerformed by Means of Coaxial Bopsy System with an Eccentric Drill, Radiology, pp. 549-552, Aug. 1993.
Gunal et al., Compartment Syndrome After Intraosseous Infusion: An Expiremental Study in Dogs, Journal of Pediatric Surgery, vol. 31, No. 11, pp. 1491-1493.
BioAccess.com, Single Use Small Bone Power Tool—How It Works, 1 pg.
Vidacare Corporation Comments to Intraosseous Vascular Access Position Paper, Infusion Nurses Society, 6 pages, May 4, 2009.

\* cited by examiner

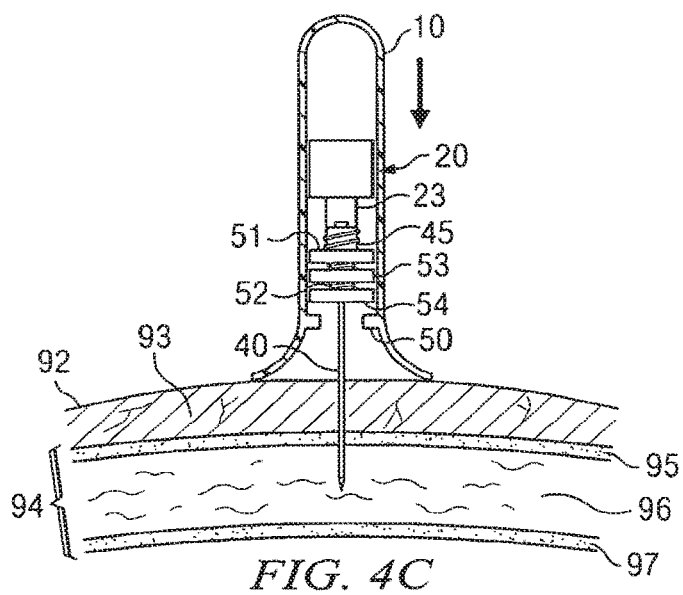
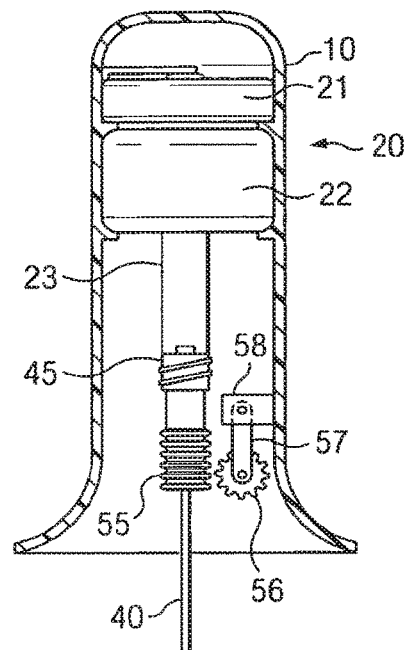
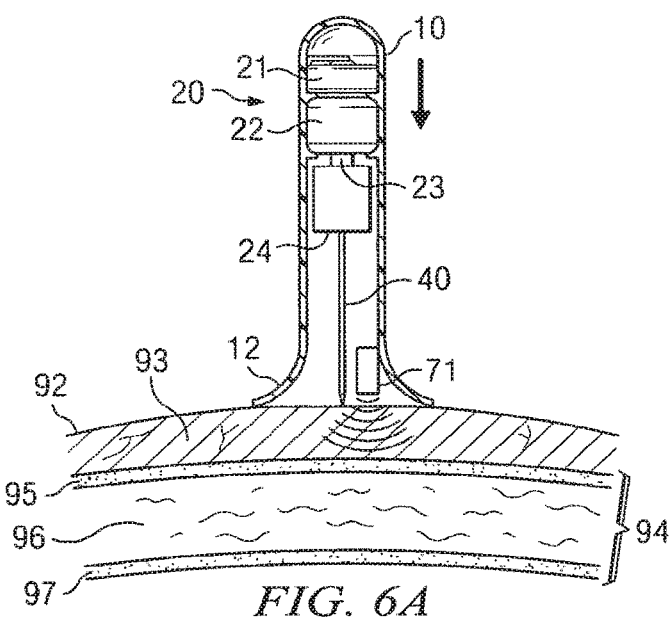
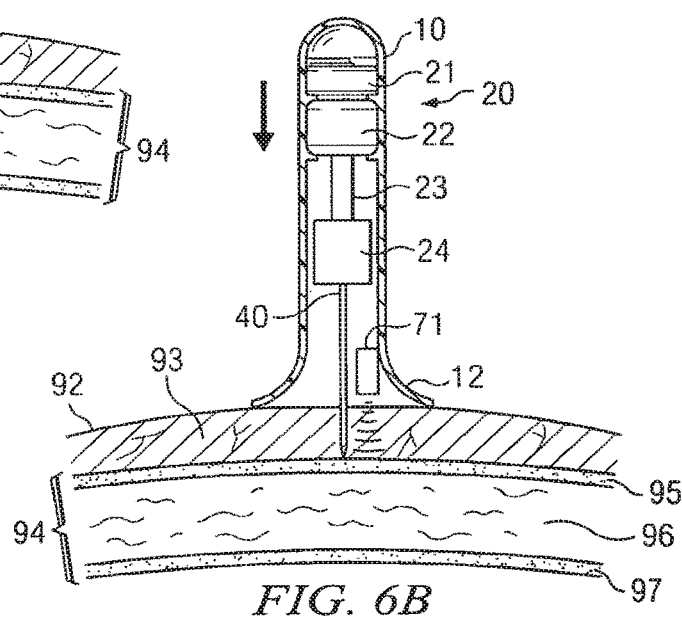

APPARATUS FOR ACCESSING BONE MARROW INCLUDING DEPTH CONTROL MECHANISM

RELATED APPLICATION

This application is a continuation application of U.S. patent application Ser. No. 11/023,173, filed Dec. 27, 2004, now U.S. Pat. No. 9,314,228, which is a continuation of U.S. patent application Ser. No. 10/987,051, filed Nov. 12, 2004, now U.S. Pat. No. 8,142,365, which claims priority to U.S. Provisional Patent Application No. 60/519,462, filed Nov. 12, 2003, which also claims foreign priority to Taiwan Patent Application No. 93134480, filed Nov. 11, 2004, and which is also a continuation-in-part application of U.S. patent application Ser. No. 10/449,503, filed May 30, 2003, now U.S. Pat. No. 7,670,328, which claims priority to U.S. Provisional Patent Application No. 60/384,756, filed May 31, 2002, the contents of which are hereby incorporated in their entirety by reference.

TECHNICAL FIELD

The present invention is related in general to an apparatus and method to access the bone marrow and specifically to an apparatus and method for accessing the bone marrow of a human's sternum.

BACKGROUND OF THE INVENTION

Every year, millions of patients are treated for life-threatening emergencies in the United States. Such emergencies include shock, trauma, cardiac arrest, drug overdoses, diabetic ketoacidosis, arrhythmias, burns, and status epilepticus just to name a few. For example, according to the American Heart Association, more than 1,500,000 patients suffer from heart attacks (myocardial infarctions) every year, with over 500,000 of them dying from its devastating complications. In addition, many wounded soldiers die unnecessarily because intravenous (IV) access cannot be achieved in a timely manner. Many soldiers die within an hour of injury, usually from severe bleeding and/or shock.

An essential element for treating all such emergencies is the rapid establishment of an IV line in order to administer drugs and fluids directly into the circulatory system. Whether in the ambulance by paramedics, in the emergency room by emergency specialists or on the battlefield by an Army medic, the goal is the same—to start an IV in order to administer life-saving drugs and fluids. To a large degree, the ability to successfully treat such critical emergencies is dependent on the skill and luck of the operator in accomplishing vascular access. While it is relatively easy to start an IV on some patients, doctors, nurses and paramedics often experience great difficulty establishing IV access in approximately 20 percent of patients. The success rate on the battlefield is much lower where Army medics are only about 29 percent successful in starting an IV line during emergency conditions in the field. These patients are probed repeatedly with sharp needles in an attempt to solve this problem and may require an invasive procedure to finally establish an intravenous route.

In the case of patients with chronic disease or the elderly, the availability of easily-accessible veins may be depleted. Other patients may have no available IV sites due to anatomical scarcity of peripheral veins, obesity, extreme dehydration or previous IV drug use. For these patients, finding a suitable site for administering lifesaving drugs becomes a monumental and frustrating task. While morbidity and mortality statistics are not generally available, it is known that many patients with life-threatening emergencies have died of ensuing complications because access to the vascular system with life-saving IV therapy was delayed or simply not possible. For such patients, an alternative approach is required.

The intraosseous (IO) space provides a direct conduit to the systemic circulation and, therefore, is an attractive alternate route to administer IV drugs and fluids. Intraosseous infusion has long been the standard of care in pediatric emergencies when rapid IV access is not possible. The military used hand-driven IO needles for infusions extensively and successfully during World War II, but the needles were cumbersome, difficult to use, and often had to be driven into the bone. Drugs administered intraosseously enter the circulation as rapidly as they do when given intravenously. In essence, the bone marrow is considered to be a large non-collapsible vein.

Although effective in achieving IO access, the currently available IO infusion devices suffer from several significant limitations. Current devices are single-use only and bulky, which limits the number of devices a medic can take into the field. Manually inserted IO needles are very difficult to use in hard adult bones. Current devices frequently penetrate not only the anterior bone cortex, but may also the posterior cortex. In addition, some current devices pose a significant risk of shattering the bone upon use. After the needle is inserted, many current devices suffer from a high rate of dislodgement from the bone because of the non-axial manner in which they must be inserted. Dislodgement often leads to extravasation (leakage of fluid from the entry points of the needle).

SUMMARY OF THE INVENTION

In accordance with teachings of the present invention, various embodiments of an apparatus to access the bone marrow of a human's sternum are provided including various embodiments of a means to control depth of penetration into the bone marrow. In some embodiments, an apparatus of the invention includes a tissue penetrator configured to penetrate the sternum, a power mechanism operable to drive the tissue penetrator into the sternum (driver), and a depth control mechanism operable to control the depth of penetration of the tissue penetrator into the sternum. The tissue penetrator may include a pressure-sensitive probe capable of transmitting pressure changes to a sensor within the apparatus. The power mechanism may include axial force delivered by an operator. A driver may include a power source selected from the group consisting of a motor, a battery, a coded spring, compressed gas, and a solar power cell. A tissue penetrator may include an outer cannula and an inner trocar. A tissue penetrator assembly may include a tissue penetrator, a connector such as a luer lock, a collar, and/or a blade. A depth control mechanism may include a trigger, physical stops at preset positions, a revolutions-per-minute (RPM) sensor, a torque sensor, a power sensor, a reverse clutch, a gear, an ultrasound sensor, and/or a depth probe or sensor. A trigger may be operably connected to the motor and/or a switch such that upon meeting a preset condition (e.g. change in RPM or torque, change in power consumption, physical contact with bone), tissue penetrator advancement is either terminated or proceeds to a preset depth level.

According to some embodiments of the invention, the driving force for tissue penetration is derived in whole or in part from the application of pressure by the operator. The applied pressure may activate a driver according to the invention. When the applied pressure surpasses a preset threshold, it may engage a manual driver means whereby operator action (e.g. pressure or movement) directly advances the tissue penetrator.

The present invention also provides a tissue penetrator that includes a means, whereby the tissue penetrator itself serves as the depth probe. Thus, the tissue penetrator itself may include a sensor operably linked to a trigger that, in turn, is operably linked to the driver.

In addition, the present invention provides a method of rapidly establishing access to intraosseous circulation via the intraosseous space including contacting a subject with an apparatus having a tissue penetrator configured to penetrate the sternum, a driver operable to drive the tissue penetrator into the sternum, and a depth control mechanism operable to control the depth of penetration of the tissue penetrator into the sternum and deploying the tissue penetrator.

BRIEF DESCRIPTION OF THE DRAWINGS

A more complete and thorough understanding of the present embodiments and advantages thereof may be acquired by referring to the following description taken in conjunction with the accompanying drawings, in which like reference numbers indicate like features, and wherein:

FIG. 4C is a schematic drawing of the apparatus and sternum shown in FIG. 4A, wherein the tissue penetrator has penetrated the skin, muscle, and anterior cortex and entered the intraosseous space;

FIG. 5 is a schematic drawing showing an elevation view of a tissue penetrator having a depth control mechanism actuated by a gear in accordance with the teachings of the present invention;

FIG. 6A is a schematic drawing showing a longitudinal cross-section of an apparatus for accessing, sternal bone marrow and a human sternum, wherein the apparatus is positioned on the skin of a human at the location shown in FIG. 1;

FIG. 6B is a schematic drawing of the apparatus and sternum shown in FIG. 6A, wherein the tissue penetrator has penetrated the skin and muscle;

DETAILED DESCRIPTION OF THE INVENTION

Figure 1:
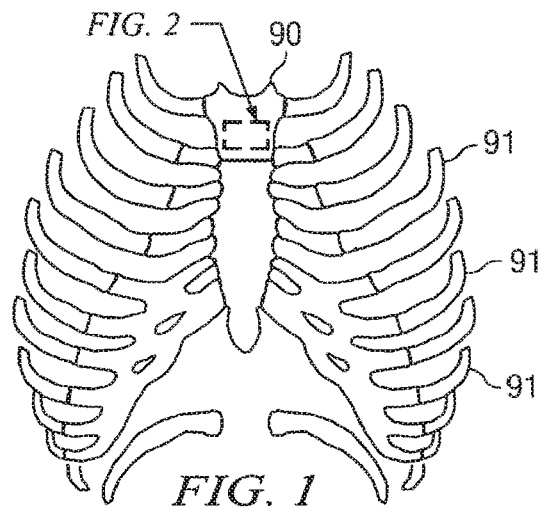
FIG. 1 is a schematic drawing showing the gross bone stmcture of the sternocostal region of a human.

Some preferred embodiments of the invention and its advantages are best understood by reference to FIGS. 1-17B wherein like numbers refer to same and like parts. Table 1 lists reference numerals with their associated names and figures in which they appear.

TABLE 1

| No. | Feature Name | FIGS. |
|---|---|---|
| 10 | housing | 2A, 2B, 3A, 3B, 4A, 4B, 4C, 6A, 6B, 6C, 7, 8, 9A, 16A, 16B, 16C, 16D, 17A, 17B |
| 11 | cassette housing | 16A, 16B, 16C, 16D, 16E |
| 12 | flange | 2A, 2B, 3A, 3B, 4A, 6A, 6B, 6C, 7, 8, 9A, 16A, 16B, 16C, 16D, 17A |
| 13 | support member | 16A, 16B, 16C, 16D, 16E |
| 14 | end member | 16A, 16B, 16C, 16D, 16E |
| 15 | cartridge | 16A, 16E |
| 16 | detent | 16A, 16E |
| 17 | engaging lock | 16A |
| 18 | needle shield | 16A, 16B |
| 19 | reusable handle | 16A, 16B, 16C, 16D |
| 20 | driver | 2A, 2B, 3A, 3B, 4A, 4B, 4C, 6A, 6B, 7, 8 |
| 21 | battery | 2A, 2B, 5, 6A, 6B, 6C, 7, 8, 9A |
| 22 | motor | 2A, 2B, 5, 6A, 6B, 6C, 7, 8, 9A |
| 23 | drive shaft | 2A, 2B, 4A, 4B, 4C, 5, 6A, 6B, 6C, 7, 8, 9A, 9B, 9C |
| 24 | coupling end | 2A, 2B, 6A, 6B, 6C, 7, 8 |
| 25 | spring | 3A, 3B, 16A, 16B, 16C, 16D, 17A, 17B |
| 26 | coupling end | 3A, 3B |
| 30 | tissue penetrator assembly | 14B, 17B |
| 31 | hub | 14B, 17A, 17B, 17C |
| 32 | flange | 14B, 17A, 17B, 17C |
| 33 | screw | 14B, 17A, 17B, 17C |
| 34 | blade | 15A, 15B, 15C, 15D |
| 35 | retraction lever | 15A, 15C, 15D |
| 40 | tissue penetrator | 2A, 2B, 3A, 3B, 4A, 4B, 4C, 5, 6A, 6B, 6C, 7, 8, 9A, 9B, 9C, 15A, 15C, 15D, 16A, 16B, 16C, 16D, 16E, 17A, 17B, 17C |
| 41 | cannula | 14A, 14B, 15B |
| 42 | trocar | 10A, 10B, 14A, 14B, 15B |
| 43 | collar | 14A, 15A, 15C, 15D |
| 44 | sliding collar | 8 |
| 45 | connector | 4A, 4B, 4C, 5, 14B, 16A, 16E, 17A, 17B, 17C |
| 46 | central line | 10A, 10B, 11, 15B |
| 50 | annular stop | 2A, 2B, 3A, 3B, 4A, 4B, 4C |
| 51 | first penetrator shoulder | 4A, 4B, 4C |
| 52 | threaded annulus | 4A, 4B, 4C |
| 53 | second penetrator shoulder | 4A, 4B, 4C |
| 54 | third penetrator shoulder | 4A, 4B, 4C |
| 55 | ribs | 5 |
| 56 | gear | 5 |
| 57 | suspension member | 5 |
| 58 | support annulus | 5 |
| 60 | vertical clutch drive member | 9A, 9B, 9C |
| 61 | vertical clutch flywheel | 9A, 9B, 9C |
| 62 | vertical engaging pin | 9A, 9B, 9C |
| 63 | concentric clutch drive member | 10A, 10B |
| 64 | concentric clutch flywheel | 10A, 10B, 11 |
| 65 | horizontal engaging pin | 10A, 10B, 11 |
| 66 | pawl | 10A, 10B, 11 |
| 67 | coil spring | 10A, 10B, 11 |
| 68 | leaf spring | 11 |
| 70 | probe | 7, 16A, 16B, 16C, 16D, 16E |
| 71 | ultrasonic sensor | 6A, 6B, 6C |
| 90 | sternum | 1 |
| 91 | ribs | 1 |
| 92 | skin | 2A, 2E, 3A, 3B, 4A, 4B, 4C, 6A, 6B, 6C, 7, 8, 9A, 14B, 15A, 15C, 15D, 16C, 16D, 16E, 17A, 17B, 17C |

TABLE 1-continued

| No. | Feature Name | FIGS. |
|---|---|---|
| 93 | muscle | 2A, 2B, 3A, 3B, 4A, 4B, 4C, 6A, 6B, 6C, 7, 8, 9A, 14B, 15A, 15C, 15D, 16C, 16D, 16E, 17A, 17B, 17C |
| 94 | bone | 2A, 2B, 3A, 3B, 4A, 4B, 4C, 6A, 6B, 6C, 7, 8, 9A, 14B, 15C, 15D, 16D, 17A, 17B |
| 95 | anterior cortex | 2A, 2B, 3A, 3B, 4A, 4B, 4C, 6A, 6B, 6C, 7, 8, 9A, 14B, 15A, 15C, 15D, 16D, 17A, 17B |
| 96 | intraosseous space | 2A, 2B, 3A, 3B, 4A, 4B, 4C, 6A, 6B, 6C, 7, 8, 9A, 14B, 15A, 15C, 15D, 16D, 17A, 17B |
| 97 | posterior cortex | 2A, 2B, 3A, 3B, 4A, 4B, 4C, 6A, 6B, 6C, 7, 8, 9A, 14B, 16D, 17A, 17B |

The sternum, as shown in FIG. 1, is a flat, narrow bone comprising three segments, the manubrium, the gladiolus, and the xiphoid process. Each segment includes an intraosseous space bounded by compact bone. According to the present invention, the intraosseous space is the region where cancellous bone and the medullary cavity combine. Bone marrow includes blood, blood forming cells, and connective tissue found in the intraosseous space. For purposes of illustration, compact bone that is nearer to the anterior or dorsal surface shall be referred to as "anterior compact bone" or "anterior bone cortex" and compact bone that is farther from the dorsal or anterior surface shall be referred to as "posterior compact bone" or "posterior bone cortex."

According to one non-limiting embodiment, an apparatus of the invention may include (a) a driver operable to drive at least a portion of a tissue penetrator into the intraosseous space, (b) a tissue penetrator configured to penetrate the anterior cortex of a sternum, and (c) a depth control mechanism operable to control the depth of penetration of the tissue penetrator into the sternum. For example, in some embodiments, the depth control mechanism may include a pressure-sensing tissue penetrator that transmits pressure changes on insertion to a sensor. The sensor then activates a trigger which in turn activates a motor or other mechanism to cause the tissue penetrator to insert into the intraosseous space a pre-selected depth.

Devices of the invention may be configured in any convenient form. For example, in some embodiments, the tissue penetrator, driver, and depth control mechanism may be arranged in separate housings or bundled in a single housing. Housings of the invention may be formed in any suitable configuration including, without limitation, shapes like a cylinder, a barrel, a bullet, a carpenter's drill, a pistol, or any other convenient form.

Driver

The driver provides power to the tissue penetrator. The power to penetrate the skin, muscle, and anterior cortex may be supplied to the tissue penetrator by any suitable means including, without limitation, one or more of the following: a battery, a spring, compressed gas, manual force, and any other mechanical or electrical source of rotation or reciprocation. The power may also be supplied directly or indirectly (e.g. using gears) by the operator and/or the patient. In addition to batteries, electric power may come from any other suitable source including conventional hospital or home wall outlets. The power source may be operably coupled with a motor. Motors of the invention may be selected from the group consisting of DC motors, AC motors, compressed gas motors, wound spring motors, and reciprocating motors. Motors of the invention may also be coupled to one or more gears, which may optionally be positioned in one or more gear boxes.

Figure 2A:
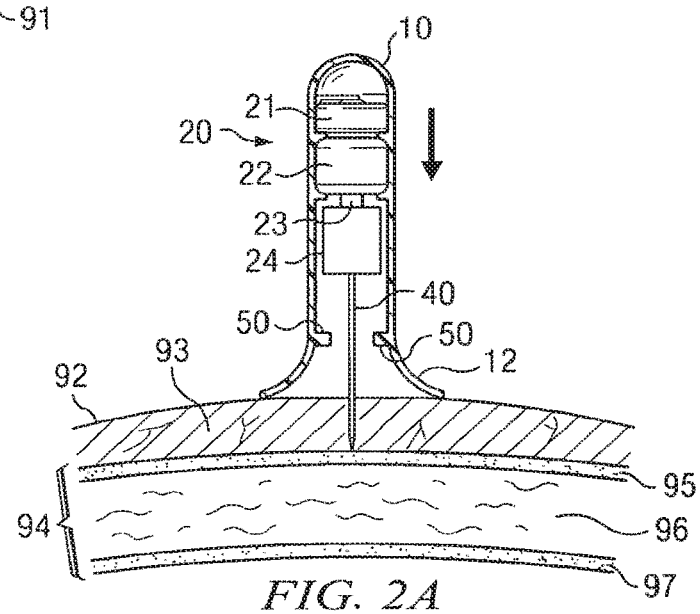
FIG. 2A is a schematic drawing showing a longitudinal cross-section of an apparatus for accessing sternal bone marrow and a human sternum, wherein the apparatus is positioned on the skin of a human at the location shown in FIG. 1 and the tissue penetrator has penetrated the skin and muscle.
Figure 2B:
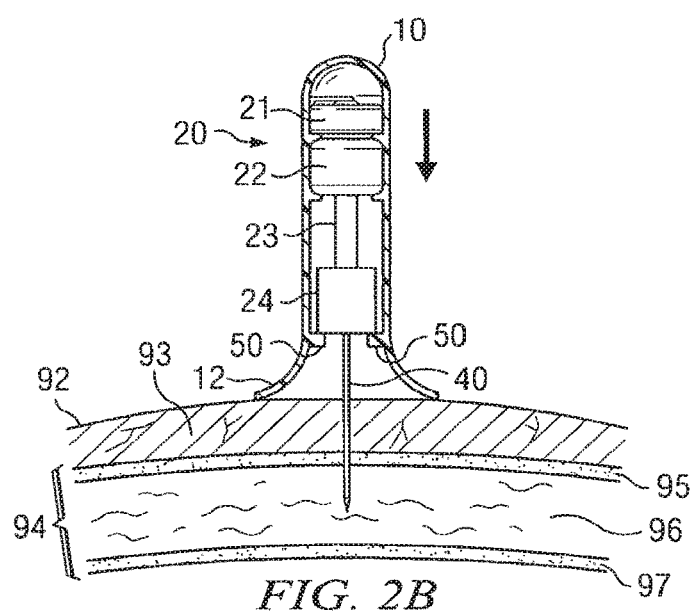
FIG. 2B is a schematic drawing of the apparatus and sternum shown in FIG. 2A, wherein the tissue penetrator has penetrated the skin, muscle, and anterior cortex and entered the intraosseous space.

According to the embodiment of the invention shown in FIGS. 2A and 2B, driver 20 includes battery 21 and motor 22 that are electrically coupled and contained within housing 10. Driver 20 also includes drive shaft 23 operably linked to motor 22. Driver 20 further includes coupling end 24 attached to drive shaft 23. Coupling end 24 in this and other embodiments may include a gear box. Similarly, FIGS. 6A, 6B, 6C, 7, 8, 9A, and 14B show other embodiments in which the driver may include like batteries, motors, and drive shafts.

Figure 3A:
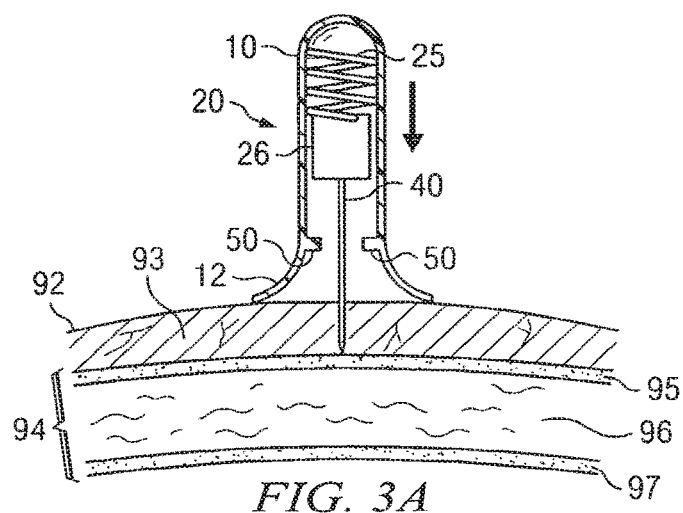
FIG. 3A is a schematic drawing showing a longitudinal cross-section of an apparatus for accessing sternal bone marrow and a human sternum, wherein the apparatus is positioned on the skin of a human at the location shown in FIG. 1 and the tissue penetrator has penetrated the skin and muscle.
Figure 3B:
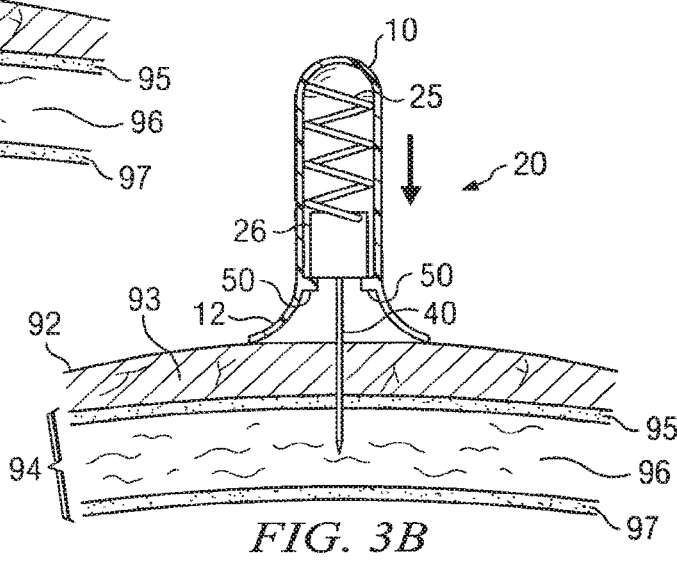
FIG. 3B is a schematic drawing of the apparatus and sternum shown in FIG. 3A, wherein the tissue penetrator has penetrated the skin, muscle, and anterior cortex and entered the intraosseous space.

According to the embodiment of the invention shown in FIGS. 3A and 3B, driver 20 includes spring 25 and coupling end 26 wherein spring 25 and coupling end 26 are connected and contained within housing 10. By contrast, according to the embodiment shown in FIGS. 16A, 16B, 16C, 16B, 17A, and 17B, driver 20 includes spring 25 without a connecting member. Spring 25 may be directly or indirectly coupled to the closed-end of the housing fixing the position of that end of spring 25. In some embodiments of the invention, coupling end 26 may further include a trigger mechanism for releasably holding spring 25 in a compressed "ready" position, a sensor for detecting pressure changes from the tissue penetrator and any other necessary relay circuit required to activate the trigger and or driver.

Tissue Penetrator

Typically, a tissue penetrator will include an outer sheath, such as a needle and an inner trocar. Tissue penetrators of the invention may include in various combinations a needle, a needle set, a cannula, a trocar, a stylet, a catheter, or combinations thereof. Needles that are suitable for use in the present invention may be from about twenty gauge to about ten gauge. In some preferred embodiments, a tissue penetrator includes an outer needle or cannula and an inner trocar or stylet. In these embodiments, the trocar or stylet may prevent clogging of the needle by bone fragments during the drilling process. The tissue penetrator may include a needle set in which the component trocar and cannula are ground together to produce a matched set of a specific design to facilitate passage through bone.

According to the invention, a tissue penetrator assembly includes a tissue penetrator. It may further include a collar, a connector, a hub, and combinations thereof. Collars of the invention, when present, may serve as depth control mechanisms. Connectors or hubs may serve as a means to connect an inserted catheter to a source of fluids or drugs including without limitation, blood, intravenous fluids of various formulations and any other fluid or medication suitable for intravenous administration.

In some embodiments, a connector or hub may be any structure that supports or permits unidirectional or bidirectional access to the intraosseous space. Connectors may include one or more locking mechanisms to prevent accidental disconnections between a source of intravenous fluid and the inserted cannula. Connectors such as Luer locks may be male or female. In some preferred embodiments, a connector is a leer lock.

According to the present invention, a tissue penetrator assembly may further include a hub with a flange to protect the skin and to stabilize the device after insertion into a human's sternum. The hub also provides a handle to remove the IO needle after use. The hub flange is the flat end of the hub that is nearer to the skin. Hubs may be made of any material, preferably a material that may be rendered sterile.

Figure 14A:
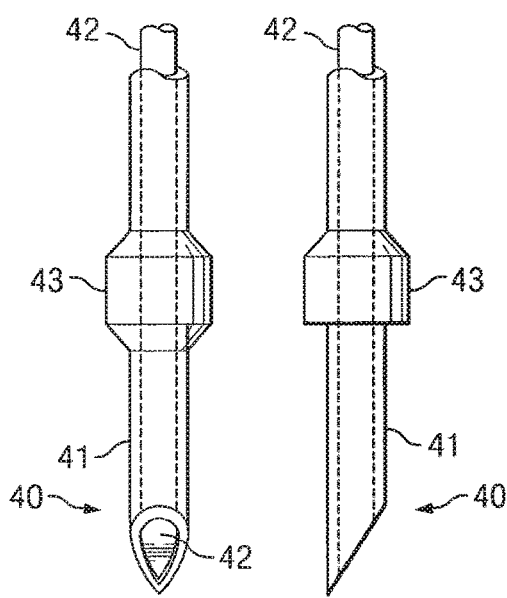
FIG. 14A is a schematic drawing showing an elevation view of intraosseous tissue penetrators with collars according to the teachings of the present invention.
Figure 14B:
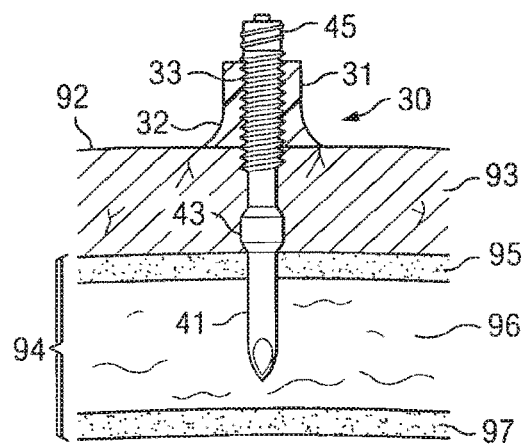
FIG. 14B is a schematic drawing showing a longitudinal cross-section of an apparatus for accessing sternal bone marrow a human sternum, wherein the apparatus is positioned on the skin of a human at the location shown in FIG. 1 and the tissue penetrator has penetrated the skin, muscle, and anterior cortex and entered the intraosseous space.

In one specific embodiment, shown in FIG. 14B tissue penetrator assembly 30 includes connector 45, hub 31 with flange 32, screw 33, cannula 41 and collar 43. As shown, the stylet has been removed.

In some embodiments of the invention, the tissue penetrator may be propelled into the IO space without rotation. This may be by direct manual force, or by a reciprocating action. In some embodiments, the needle may be rotated about its longitudinal axis in order to facilitate entry into the IO space. The needle may be rotated even where a driver including a spring is used. One way to rotate a spring-driven needle is to rotatably couple it with the housing. For example, a spring-driven needle may be fixedly attached to a coupling end having male threads on its outer circumference. This coupling end may be mated with a housing with corresponding female threads on its inner circumference. Consequently, as the spring propels the coupling end and attached needle through the housing, the coupling end would rotate. A swing may also be used to drive a tissue penetrator into the IO space by an impact force without rotation.

As a further aid to IO entry, a small incision may be made in the patient's skin at the site where IO entry is desired. For example, if a collar is included with the apparatus, a skin incision will facilitate passage of the tissue penetrator to the bone. The incision may be formed using any suitable surgical blade, which may optionally form part of the tissue penetrator assembly. One or more blades may be included. Blades may be configured to be collapsible, removable, or retractable.

Figure 15A:
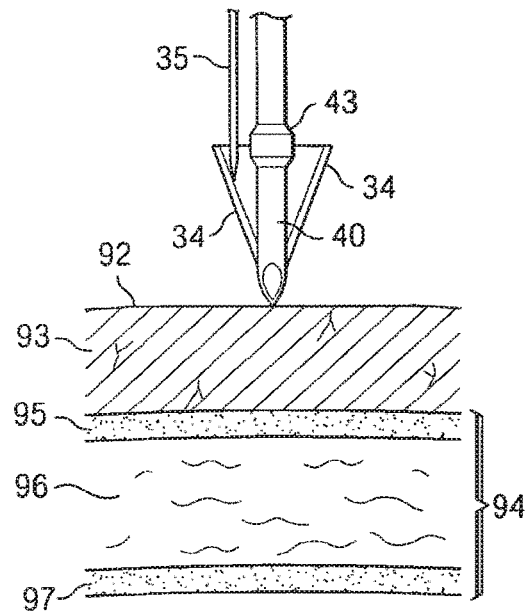
FIG. 15A is a schematic drawing showing a longitudinal cross-section of an intraosseous tissue penetrator assembly with a built-in blade according to the teachings of the present invention and a human sternum, wherein the assembly is positioned on the skin of a human at the location shown in FIG. 1 and the tissue penetrator has not penetrated the skin.
Figure 15B:
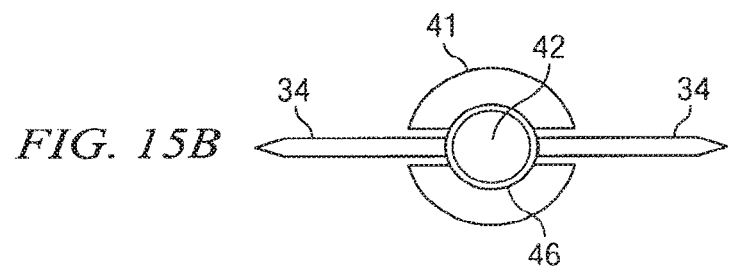
FIG. 15B is a schematic drawing showing a radial cross-section of the tissue penetrator assembly shown in FIG. 15A.
Figure 15C:
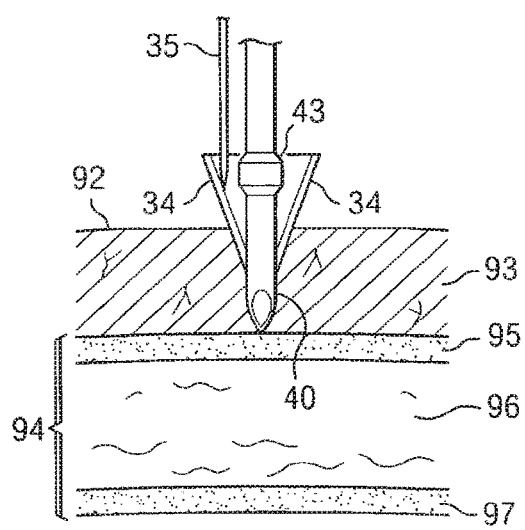
FIG. 15C is a schematic drawing showing a longitudinal cross-section of the tissue penetrator assembly shown in FIG. 15A and a human sternum, wherein the tissue penetrator has penetrated the skin and muscle and the blade has penetrated the skin.
Figure 15D:
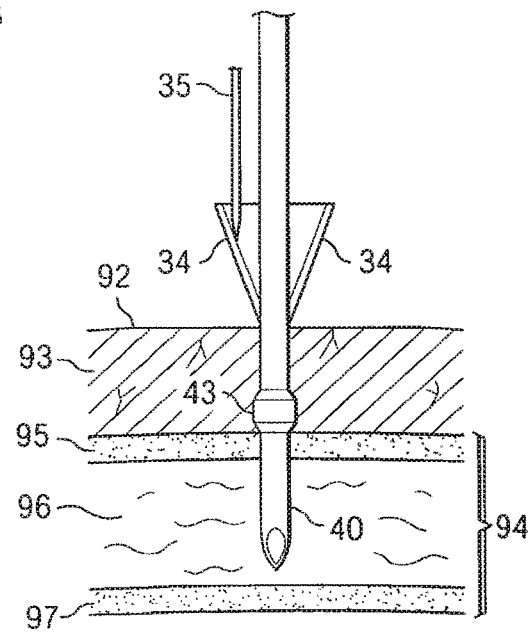
FIG. 15D is a schematic drawing showing a longitudinal cross-section of the tissue penetrator assembly shown in FIG. 1, and a human sternum, wherein the tissue penetrator has penetrated the skin, muscle, and anterior cortex and entered the intraosseous space and wherein the blade is in its retracted position.

For example, according to the embodiment shown in FIG. 15B, retractable blade 34 is movably attached to opposite sides of cannula 41 in a plane parallel to the longitudinal axis of cannula 41. As shown in FIG. 15C, blade 34 may be used in a simple process to automatically form an incision in skin 92 at the proper place and of the proper size to permit ingress of tissue penetrator 40, which includes cannula 41 and trocar 42, and collar 43. The initial incision may be made by the needle itself as shown in FIG. 15A. The opposing blade configuration allows blade 34 to retract so that the drilling process may proceed after insertion. Retraction may be accomplished by actuating retraction lever 35 (FIG. 15D). Although not expressly shown, the opposing blade configuration may also allow the use of break-away blades that are removed after insertion, but prior to drilling.

Depth Control Mechanism

According to the teachings of the present invention, sternal IO access devices may incorporate a mechanism to prevent over-penetrating the sternum, which could potentially damage underlying structures in the chest cavity. This mechanism may include mechanical stops, electrical stops, depth detectors, and combinations thereof. An electrical stop may prevent the operator from over-drilling by interrupting drill rotation and/or advancement when it detects that the needle tip has penetrated into the sternal IO space. An electrical stop may include a pressure-sensing tissue penetrator connected to a sensor that activates a trigger to control the driver such that a tissue penetrator is inserted to a pre-selected depth in the IO space. An electrical stop may also accurately detect the location of the cortex so that the tissue penetrator may be safely advanced to a predetermined depth in the IO space. An electrical stop may include a torque detector, an ultrasound probe, a mechanical probe, or a fluid detector.

Mechanical stops include a preset drill depth (similar to a stop on a commercial drill), a collar attached to a needle or tissue penetrator, and a reverse clutch mechanism that prevents further drilling once the needle tip enters the intraosseous space of the sternum, Mechanical stops may have a fixed position or may be adjustable. If the mechanical stops are adjustable, they may be preset or adjusted while drilling is in progress. As shown in FIG. 2, annular stop 50 is a rib that traces the inner circumference of housing 10 and arrests advancement of tissue penetrator 40 by physically obstructing passage of coupling end 24. In the embodiment shown in FIG. 3, annular stop 50 obstructs passage of coupling end 26. Such physical stops may also be formed in any other suitable shape including, without limitation, arcs, bars, bumps, and ridges. Other options include a track including a groove of finite length on the inner surface of the housing and a corresponding ridge on the outer circumference of the coupling end.

The embodiment shown in FIGS. 14A and 14B illustrates that the depth of needle penetration may also be controlled by forming an enlargement or ridge around (e.g. collar) the tissue penetrator. Collar 43 is preset at the desired distance from the needle tip to assure proper placement of the device. Collar 43 may be cylindrical with symmetrically beveled ends to promote easier entry through the skin as shown in the left side of FIG. 14A or any other suitable shape and configuration necessary to achieve its purpose. Alternatively, collar 43 may have a beveled proximal end and a sheer distal end as shown in the right side of FIG. 14A. The acute angle or right angle of the distal end of collar 43 may promote a more secure stop against accidental over-penetration. The proximal end of collar 43 remains tapered to promote easy egress from the skin.

Another non-limiting embodiment of a mechanical stop is a gear that engages ridges on the drive shaft (FIG. 5) thus allowing depth control without interfering with rotation of tissue penetrator 40. Gear 56 is rotatably coupled to suspension member 57, which in turn is mounted on support 57. As shown in FIG. 5, gear 56 is disengaged from ribs 55. While not expressly pictured, gear 56 may contact and engage ribs 55 by any suitable mechanism. A gear of the invention may be configured to rotate a preset number of revolutions. Alternatively, the gear may be spring-loaded such that resistance increases with advancement, thereby creating a counter-balancing force to the driver. Devices with such gears may further reduce the possibility of penetrating or damaging the posterior cortex and underlying organs. A gear may also be operably linked to a sensor such that it may engage the drive shaft ribs 55 and stop needle advancement upon satisfaction of a pre-selected threshold.

Figure 9A:
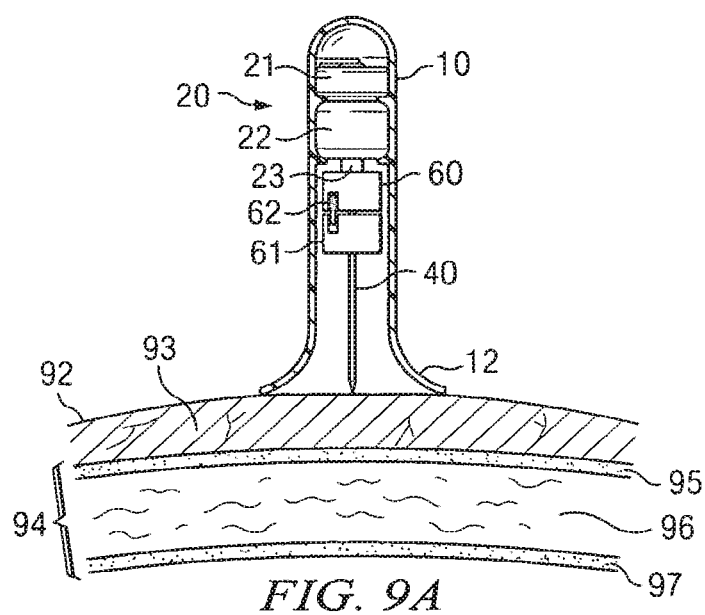
FIG. 9A is a schematic drawing showing a longitudinal cross-section of an apparatus for accessing sternal hone marrow having a vertical reverse clutch mechanism and a human sternum, wherein the apparatus is positioned on the skin of a human at the location shown in FIG. 1.
Figure 9B:
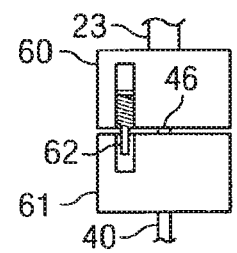
FIG. 9B is a schematic drawing showing a longitudinal cross-sectional view of the vertical reverse clutch mechanism of the apparatus shown in FIG. 9A with the vertical pin in the engaged position.
Figure 9C:
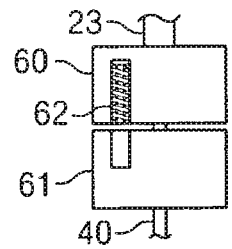
FIG. 9C is a schematic drawing showing a longitudinal cross-sectional view of the reverse clutch mechanism of the apparatus shown in FIG. 9A with the vertical pin in the disengaged position.
Figure 10A:
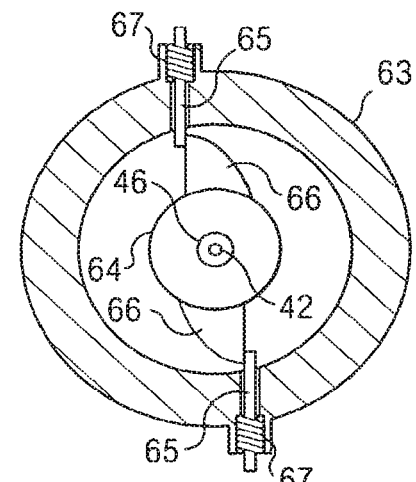
FIG. 10A is a schematic drawing of a plan view of a horizontal reverse clutch mechanism according to the teachings of the present invention wherein the horizontal pins are in the engaged position, contacting the pawls.
Figure 10B:
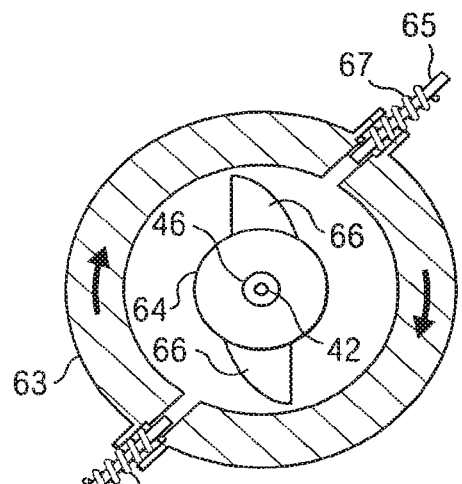
FIG. 10B is a schematic drawing of the horizontal reverse clutch mechanism shown in FIG. 10A, wherein the horizontal pins are in the disengaged position, not contacting the pawls, such that the concentric clutch flywheel comes to a rest.
Figure 11:
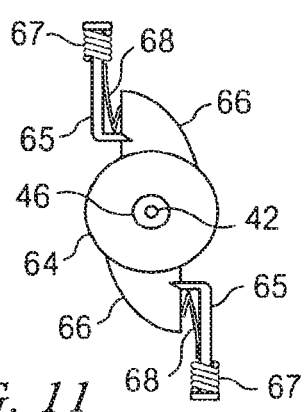
FIG. 11 is a schematic drawing of horizontal pins with leaf springs, pawls, and the shaft of a horizontal reverse clutch according to the teachings of the present invention.

The invention also provides embodiments in which a reverse clutch mechanism is used to arrest bone penetration (FIGS. 9-11). According to the embodiment of the invention shown in FIG. 9A, drive shaft 23, which is rotatably coupled with motor 21, is fixedly connected to vertical clutch drive member 60. Vertical clutch drive member 60 is releasably coupled to vertical clutch flywheel 61 by vertically engaging pin 62 (FIGS. 9A and 9B). Flywheel 61 is fixedly connected with tissue penetrator 40 such that withdrawal of vertically engaging pin 62 (FIG. 9C) interrupts the transfer of force from motor 21 to tissue penetrator 40. Accordingly, tissue penetrator 40 may come to rest due to incidental frictional forces or an active breaking mechanism.

As pictured, vertical engaging pin is spring loaded. Pin 62 may be configured to remain engaged only so long as lateral forces (torque) during the drilling process are maintained above a certain level. One may select or adjust the threshold torque required to maintain engagement, by selecting springs with a particular spring constant. As soon as the torque falls below this threshold, as it would when the needle penetrates the anterior cortex and enters the IO space, pin 62 withdraws, disengaging the driver.

The reverse clutch mechanism may also be configured as concentric rings, one embodiment of which is illustrated in FIG. 10. In these embodiments, the drive shaft may be fixedly attached to a concentric clutch drive member. Concentric clutch drive member 63 is releasably coupled to a concentric clutch flywheel 64 by horizontal engaging pins 65 and pawls 66. FIG. 10A shows an embodiment of the invention in which horizontal engaging pins 65 are engaged and concentric clutch drive member 63 rotates flywheel 64. Horizontal engaging pins 65 each include coil spring 67. When the tip of the tissue penetrator 40 has entered the IO space, horizontal engaging pins 65 withdraw from pawls 66 such that concentric clutch drive member 63 can no longer rotate flywheel 64 (FIG. 10B). Flywheel 64 and its associated tissue penetrator may then come to rest due to incidental frictional forces or an active breaking mechanism. According to some non-limiting embodiments of the invention, horizontal engaging pin 65 may further include a leaf spring 68 that releasably engages pawl 66 (FIG. 11). Both coil spring 67 and leaf spring 68 may be configured to be torque sensors.

Figure 7:
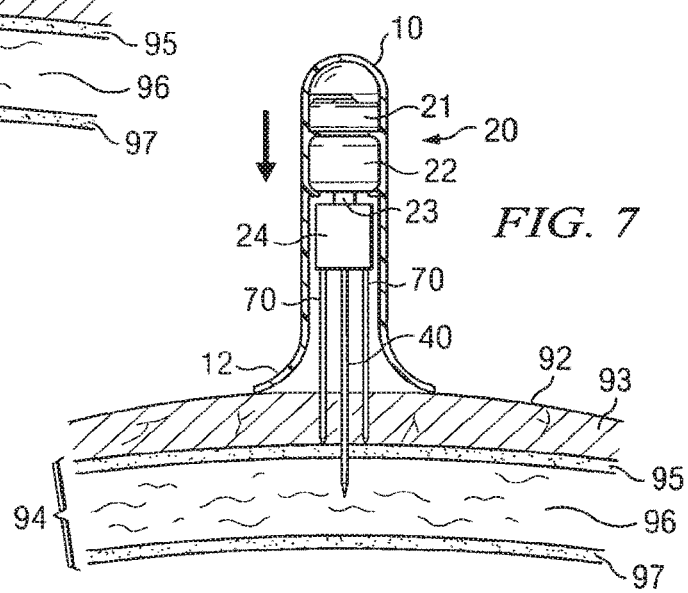
FIG. 7 is a schematic drawing showing a longitudinal cross-section of an apparatus for accessing sternal bone marrow and a human sternum, wherein the apparatus is positioned on the skin of a human at the location shown in FIG. 1, the probe has penetrated the skin and muscle, and the tissue penetrator has penetrated the skin, muscle, and anterior cortex and entered the intraosseous space.
Figure 6D:
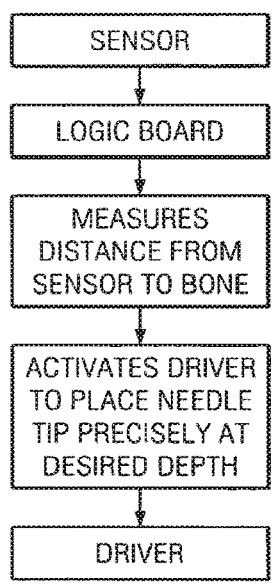
FIG. 6D is a flowchart of the signal processing between the ultrasound sensing device and driver of FIGS. 6A-6C.

Depth control mechanisms of the invention may include one or more depth sensors or probes. In one embodiment, depth sensors or probes may include pressure sensors. An example of this embodiment is shown in FIG. 7, wherein probes 70 are operably linked to coupling end 24, which may contain a pressure sensor and a trigger. Pressure on the tips of probes 70 upon contacting bone is relayed to the sensor which activates the trigger. The trigger then starts advancement of tissue penetrator 40 by activating the driver (FIG. 7). Tissue penetrator 40 may be advanced a preset distance calculated to place the tip of tissue penetrator 40 in the intraosseous space. Rotational forces (drilling), as opposed to impact forces, may be less traumatic on the bone and more precise in its application.

Figure 8:
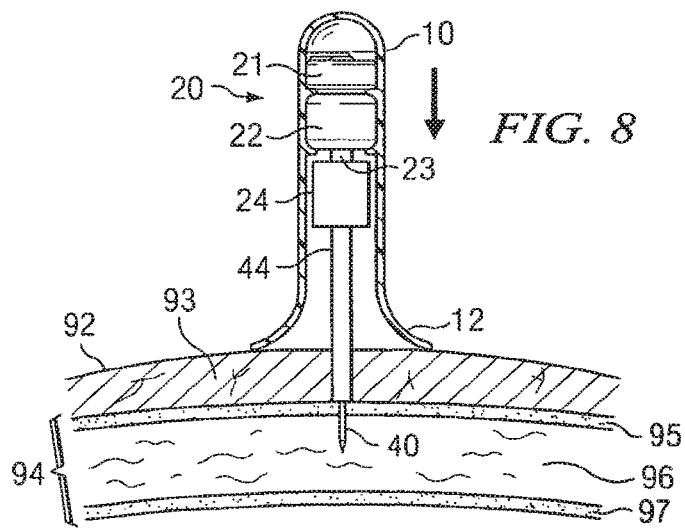
FIG. 8 is a schematic drawing showing a longitudinal cross-section of an apparatus for accessing sternal bone marrow and a human sternum, wherein the apparatus is positioned on the skin of a human at the location shown in FIG. 1, the sliding, collar has penetrated the skin and muscle, and the tissue penetrator has penetrated the skin, muscle, and anterior cortex and entered the intraosseous space.

FIG. 8 illustrates another non-limiting embodiment of a closely-fitting, cylindrical collar 44, which encloses tissue penetrator 40 that may be used to locate anterior cortex 95. Collar 44, according to this embodiment, slides relative to tissue penetrator 40 along the longitudinal axis of tissue penetrator 40. In its starting position, tissue penetrator 40 is recessed within collar 44. As shown in FIG. 8, upon making contact with anterior cortex 95, sliding collar 43 slides up into coupling end 24, which activates motor 22 to drill a predetermined distance into the bone. Motor 22 may be rotational or reciprocating. More generally, sliding collar 43 may be used to activate a driver of any kind.

Depth control using an IO device of the present invention may proceed in two stages as shown in FIG. 4. In the first stage, the needle may be advanced through the relatively soft tissues of the skin, subcutaneous tissue and muscle. In the second stage, the needle is drilled or driven through the much harder anterior cortex.

Figure 4A:
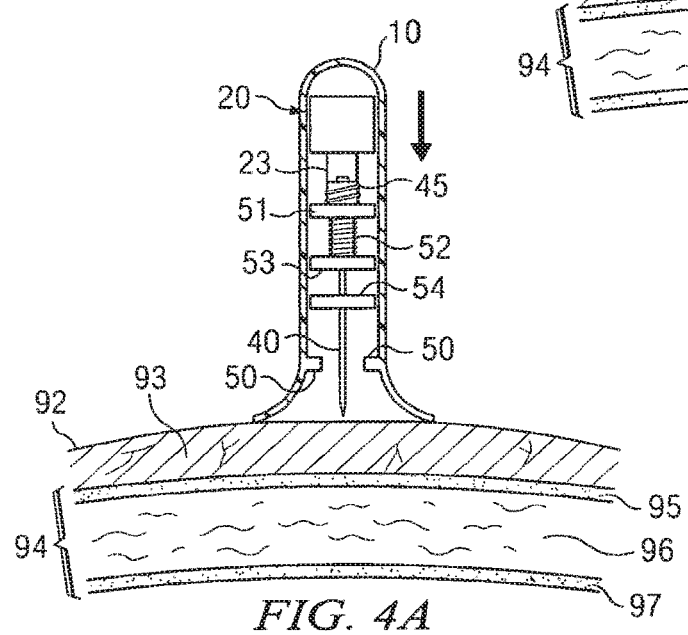
FIG. 4A is a schematic drawing showing a longitudinal cross-section of an apparatus for accessing sternal bone marrow and a human sternum, wherein the apparatus is positioned on the skin of a human at the location shown in FIG. 1.

According to the embodiment of the invention shown in FIG. 4A, the device includes housing 10, battery 21, motor 22, drive shaft 23, tissue penetrator 40, connector 45, annular stop 50, first penetration shoulder 51, threaded annulus 52, second penetration shoulder 53, and third penetration shoulder 54. The tissue penetrator assembly, according to this embodiment, includes tissue penetrator 40, connector 45, first penetration shoulder 51, threaded annulus 52, second penetration shoulder 53, and third penetration shoulder 54. The drive shaft may or may not rotate tissue penetrator 40 as it advances. Each annulus may include a pressure sensor, a trigger, or both a pressure sensor and a trigger. First penetration shoulder 51 is fixedly connected to threaded annulus 52 and drive shaft 23, Second penetration shoulder 53 is rotatably mounted on threaded annulus 52. Third penetration shoulder is slidably mounted on tissue penetrator 40. As shown, the device is in its "ready" or undeployed position.

Figure 4B:
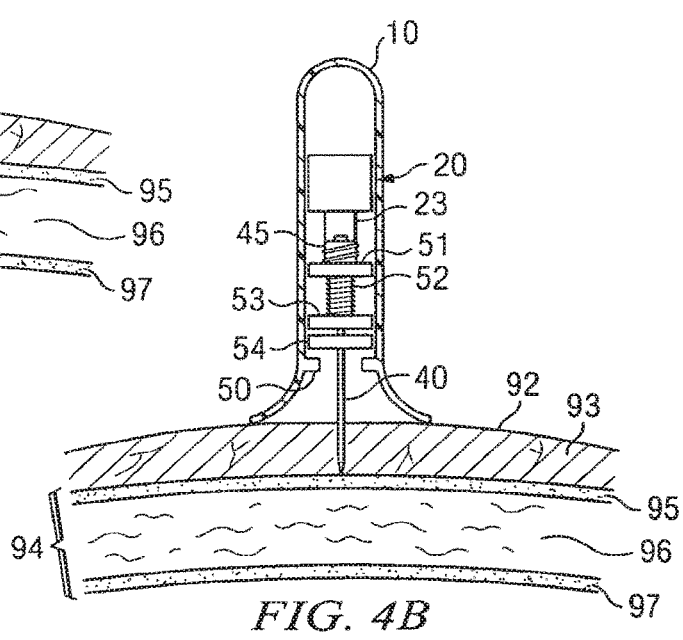
FIG. 4B is a schematic drawing of the apparatus and sternum shown in FIG. 4A, wherein the tissue penetrator has penetrated the skin and muscle.

The first stage of insertion is initiated when an operator contacts the device with the skin. Other activation methods are also possible. Upon contacting skin 92 and applying pressure, a first sensor activates advancement of the tissue penetrator assembly. As the tissue penetrator advances, third penetration shoulder 54 is stopped by annular stop 50. The rest of the tissue penetrator assembly continues to advance such that second penetration shoulder 53 contacts third penetration shoulder 54 (FIG. 4B). Concurrently, the tip of tissue penetrator 40 contacts anterior cortex 95 as shown in FIG. 4B.

This contact together with continued application of pressure by the operator initiates the second stage by triggering a second sensor to activate motor 22. Motor 22 then propels first penetration shoulder 51 the preset or operator-set distance to second penetration shoulder 53. This, in turn, advances the tip of tissue penetrator 40 through anterior cortex 95 and into IO space 96 as shown in FIG. 4C.

Depth Probes or Sensors

Devices of the present invention may include various depth probes or sensors that detect the location of the needle, the bone, or both. Sensors are preferably connected to a control mechanism (e.g. a logic board) that determines whether needle advancement shall begin, continue, or terminate. Control mechanisms may also be mechanical or triggers. Sensor detection and controller evaluation may be intermittent, periodic or continuous.

Figure 6C:
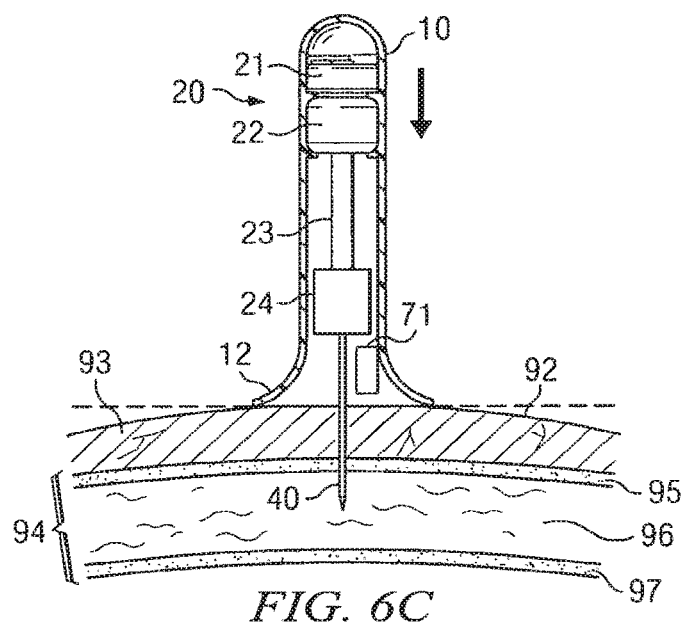
FIG. 6C is a schematic drawing of the apparatus and sternum shown in FIG. 6A, wherein the tissue penetrator has penetrated the skin, muscle, and anterior cortex and entered the intraosseous space.

For example, an ultrasonic detector may be used to locate the sternal cortex. In the non-limiting embodiment, shown in FIG. 6A, tissue penetrator 40 is in the storage or undeployed position. Ultrasonic sensor 71 detects the distance between the device (e.g. flange 12) and IO space 96. Ultrasonic sensor 71 may also detect the position of tissue penetrator 40. FIG. 6B shows tissue penetrator 40 in contact with anterior cortex 95, ready for penetration. Detection by ultrasonic sensor 71 allows the device to tailor further advancement of the cannula to the exact dimensions of the targeted bone (FIG. 6C). This may be particularly advantageous given the variability from patient to patient and variations due to compression of skin and muscle by the device operator. This signaling process is outlined in the flowchart shown in FIG. 61). Briefly, a sensor detects tissue penetrator, bone location, or both. This data is communicated to a logic board that measures or calculates the distance from the sensor to the bone. Upon obtaining this information, the driver is activated to advance the tissue penetrator the appropriate distance to achieve bone penetration.

Bone cortex is very dense requiring considerable force to penetrate. As soon as the needle or drill passes through the cortex and enters the intraosseous space a pronounced change is noted in the force required to advance the needle. Resulting changes may be a decrease in torque and an increase in motor revolutions per minute (RPM). These changes can be measured and used to switch off the motor or activate a brake to prevent additional, potentially dangerous drilling activity.

Figure 12A:
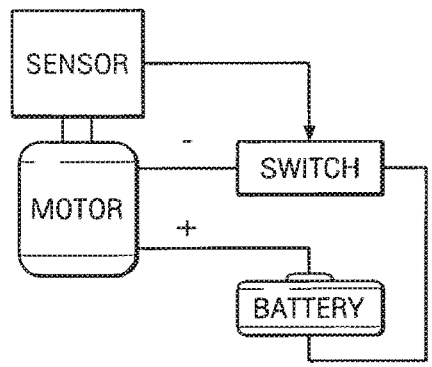
FIG. 12A is a schematic drawing of an apparatus for accessing sternal bone marrow having a torque or RPM sensor.
Figure 12B:
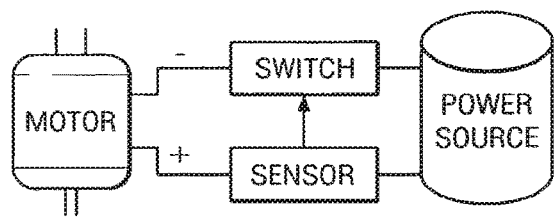
FIG. 12B is a schematic drawing of an apparatus for accessing sternal bone marrow having a power sensor.

Thus, sensors of the invention may detect torque, revolutions per minute (RPM), backpressure, power consumption or any other relevant measure of needle advancement in the embodiment shown in FIG. 12A, the sensor is mechanically coupled to the motor and detects torque and/or RPMs and activates the switch. Thus, the sensor may be a shaft encoder. By contrast, the embodiment shown in FIG. 1B the sensor is coupled to the electrical circuit between the motor and the power source and detects amperage and/or voltage.

Figure 13A:
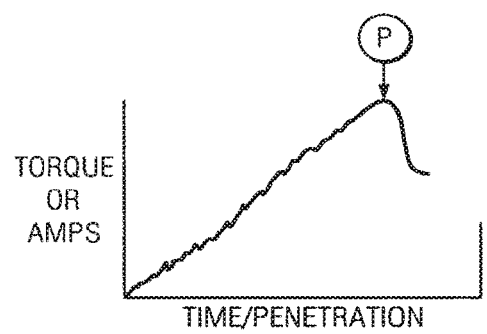
FIG. 13A is a graph showing the change in torque or amperage as a function of depth of bone penetration with the inflection point marked with an encircled "P" indicating the point at which penetration of the anterior cortex is complete.

FIG. 13A illustrates the changes in torque or amperage as a function of drilling time or depth of penetration. At the time of penetration (P), the sensor may detect the decrease in torque or amperage and may discontinues needle advancement. If the needle is rotating, a brake may be applied to bring it to rest.

Figure 13B:
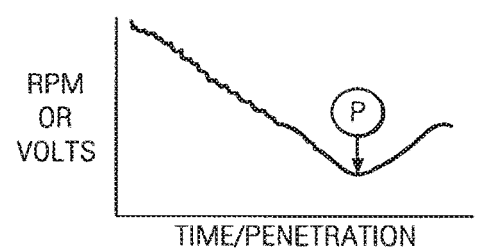
FIG. 13B is a graph showing the change in power as a function of depth of bone penetration with the inflection point marked with an encircled "P" indicating the point at which penetration of the anterior cortex is complete.

FIG. 13B illustrates the changes in RPM or voltage as a function of drilling time or depth of penetration. At the time of penetration (P), the sensor may detect the decrease in torque or amperage and may discontinues needle advancement. If the needle is rotating, a brake may be applied to bring it to rest.

Probes and sensors of the invention may be operably coupled to a driver, a tissue penetrator, a depth control mechanism, or portions or combinations thereof. In one non-limiting embodiment the tissue penetrator itself may be or include a depth probe or sensor.

Reusable Handle/Disposable Cartridge

The present invention provides intraosseous access devices with a reusable handle and a disposable cartridge containing the needle, one embodiment of which is illustrated in FIG. 16. The advantage of these devices over currently available devices is the overall size and weight reduction of carrying multiple devices in the field, such as in the medical pack by army medics. Ten (10) units of currently disposable IO devices weigh far more and take much more space than one reusable handle with 10 disposable needle assemblies. The greater part of the weight and size may be in the reusable handle. Reusable handles may contain a driver in accordance with the teachings of the present invention. Disposable cartridges may include tissue penetrator assemblies and depth sensors in accordance with the teachings of the present invention. Disposable cartridges of the invention ma engage or lock into the reusable handle with a recess and detent or any other mechanism, FIG. 16A illustrates an embodiment of an IO device of the invention including reusable handle 19 and disposable cartridge 15. This figure shows the handle separate from cartridge 15 as seen prior to connecting for use. Cartridge 15 includes tissue penetrator 40, probes 70, detent 16, coupling member 13, and end member 14. Cartridge 15 further includes releasable needle shield 18. Tissue penetrator 40 and probes 70 are covered by needle shield 18 to protect the user from accidental needle sticks and preserve tissue penetrator 40. Shield 15 may have a domed surface as shown or a flat surface to allow the cartridge to stand alone. While not shown in the figure, cartridges of the invention may further include, without limitation, hubs, flanges, screws, and bolts.

Figure 16A:
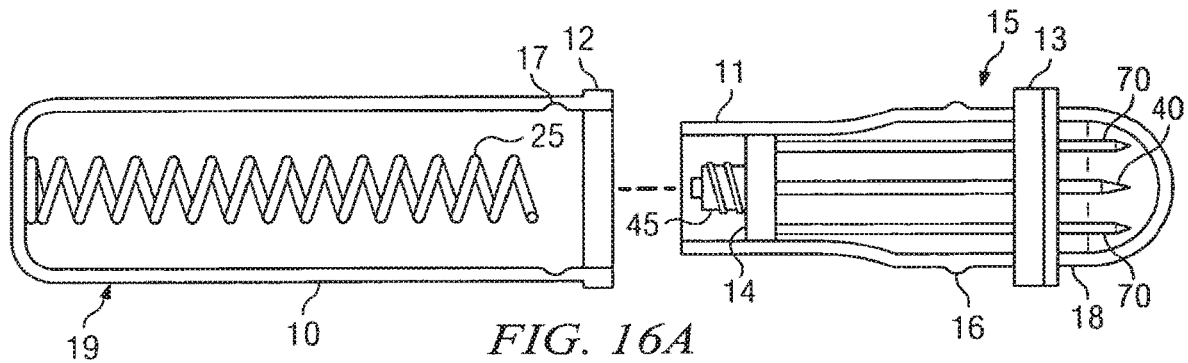
FIG. 16A is a schematic drawing showing a longitudinal cross-section of an apparatus for accessing sternal bone marrow according to the teachings of the present invention, wherein the reusable handle and the disposable cartridge are in the disengaged position and the needle shield is attached.
Figure 16B:
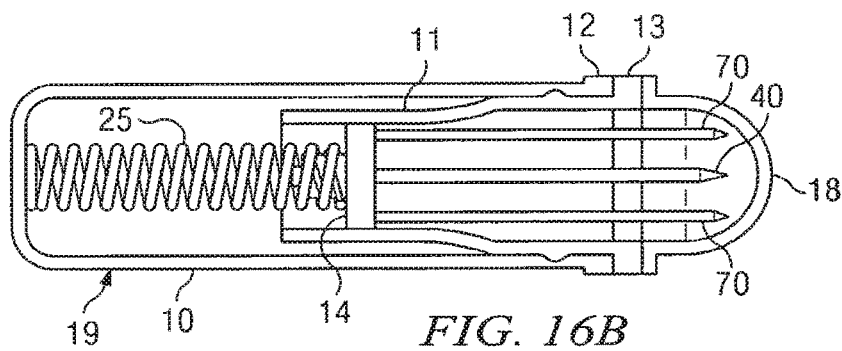
FIG. 16B is a schematic drawing showing a longitudinal cross-section of the apparatus shown in FIG. 16A, wherein the reusable handle and the disposable cartridge are in the engaged position and the needle shield is attached.
Figure 16C:
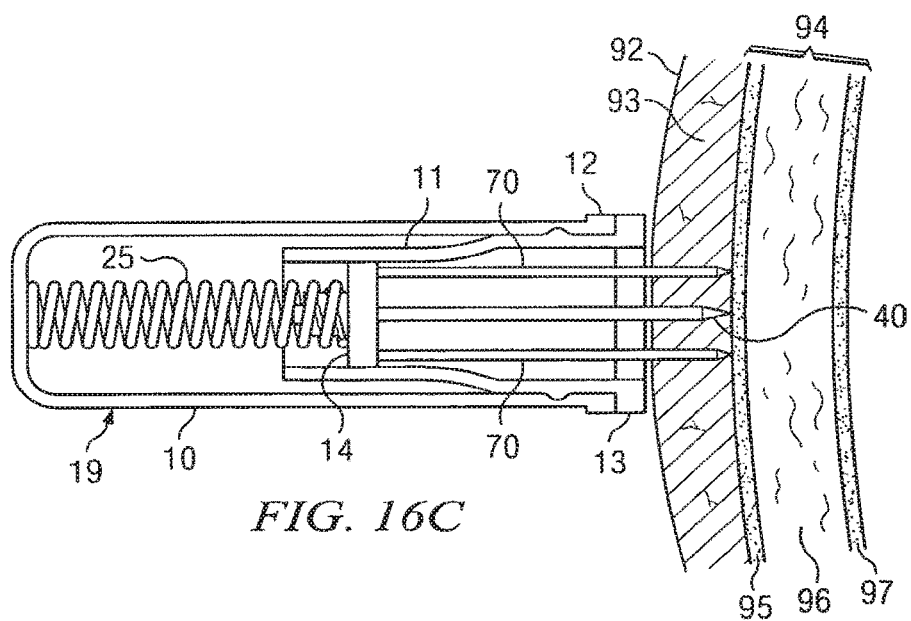
FIG. 16C is a schematic drawing showing a longitudinal cross-section of the apparatus shown in FIG. 16A, wherein the reusable handle and the disposable cartridge are in the engaged position, the needle shield is detached, and the needle and probes have been inserted into the soft tissue of a subject.
Figure 16D:
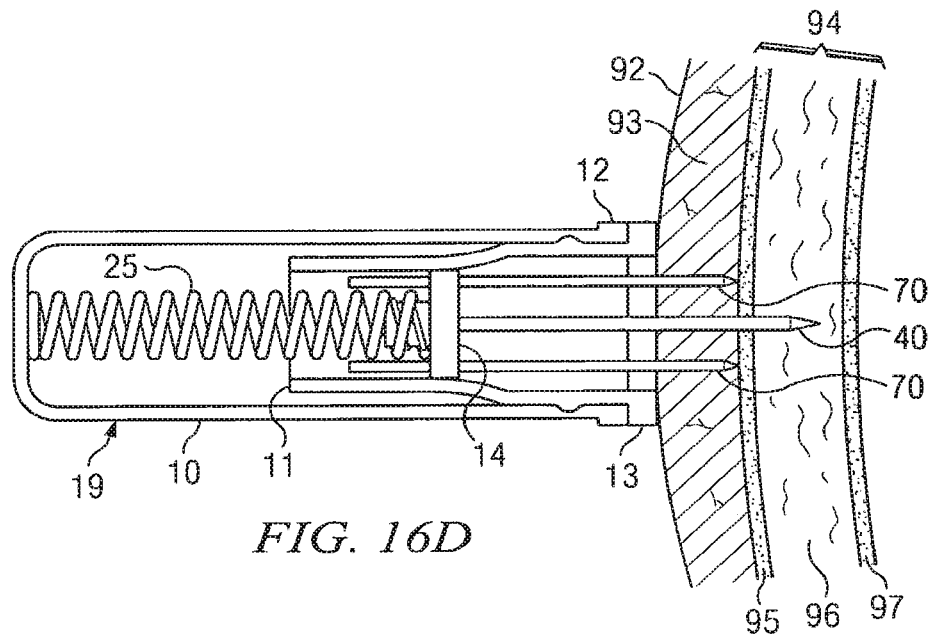
FIG. 16D is a schematic drawing showing a longitudinal cross-section of the apparatus shown in FIG. 16A and a human sternum, wherein the reusable handle and the disposable cartridge are in the deployed position, the probes have penetrated the skin and muscle, and the tissue penetrator has penetrated the skin, muscle, and anterior cortex and entered the intraosseous space.
Figure 16E:
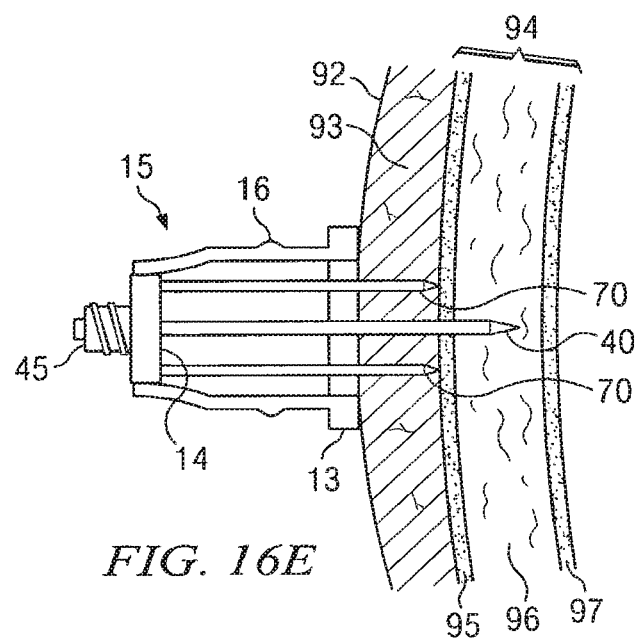
FIG. 16E is a schematic drawing showing a longitudinal cross-section of the disposable cartridge shown in FIG. 16D after the handle has been removed.

Reusable handle 19 includes housing 10, spring 25, and engaging lock 17. Engaging lock 17 engages detent 16 upon insertion of cartridge 15 into handle 19. As a result, cartridge 15 may "pop" or snap into reusable handle 19 (FIG. 16B). Although not expressly pictured, cartridge 15 and handle 19 may include a locking mechanism that is engaged by twisting cartridge 15 into handle 19. Needle shield 18 may be removed when ready for use (FIG. 16C). Deployment of tissue penetrator 40 is similar to that described for other embodiments. See e.g. FIG. 8. Briefly, compressed spring 25 is released upon probes 70 contacting anterior cortex 95. As spring 25 expands, it propels tissue penetrator 40 through anterior cortex 95 and into intraosseous space 96 (FIG. 16D). Thereafter, reusable handle 19 may be removed and a access to intraosseous space 96 may be gained through connector 44 (FIG. 16E). Spring 25 need not contact connector 45, but may contact a plate or other structi on (not expressly shown) that drives tissue penetrator 40 into bone 94.

Figure 17C:
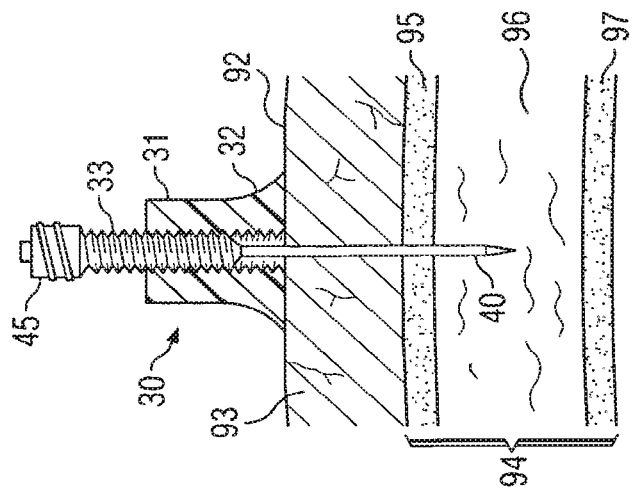
FIG. 17C is a schematic drawing showing a longitudinal cross-section of the disposable cartridge shown in FIG. 17B after the handle has been removed.
Figure 17B:
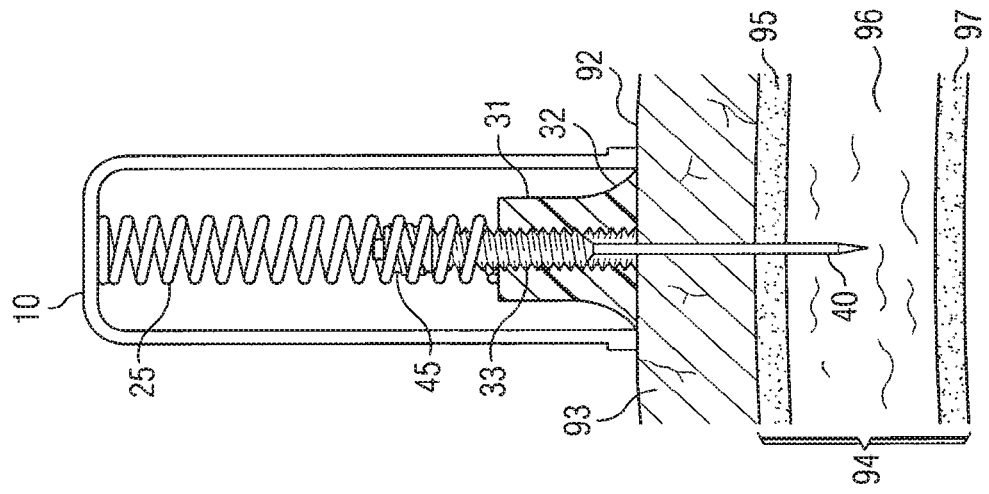
FIG. 17B is a schematic drawing showing a longitudinal cross-section of the apparatus shown in FIG. 17A, wherein the reusable handle and the disposable cartridge are in the deployed position and the tissue penetrator has penetrated the skin, muscle, and anterior cortex.
Figure 17A:
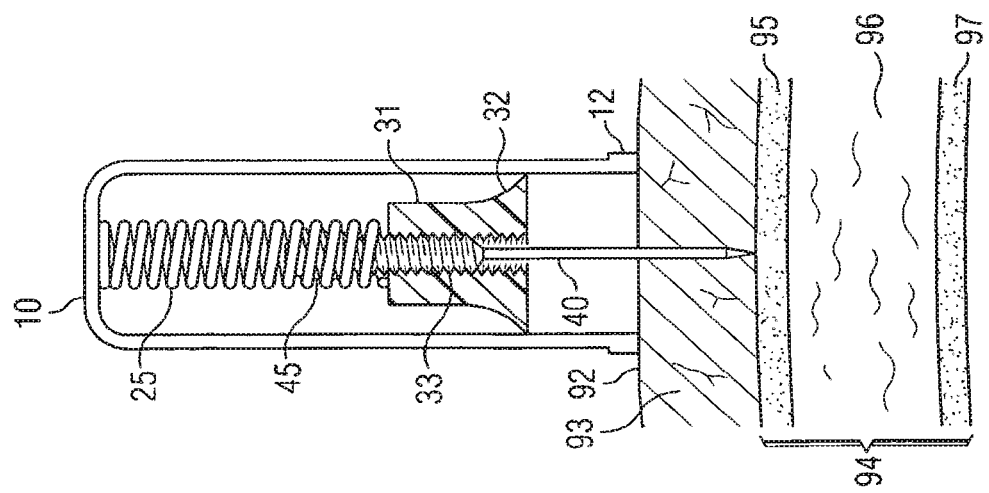
FIG. 17A is a schematic drawing showing a longitudinal cross-section of an apparatus for accessing sternal bone marrow according to the teachings of the present invention and a human sternum, wherein the reusable handle and the disposable cartridge are in the engaged position, the tissue penetrator has penetrated the skin and muscle.

As shown in FIG. 17A, a driver (here spring 25) in accordance with the invention is shown in the undeployed, ready position. Contact with skin 92 may activate the spring 25, which causes tissue penetrator 40 to penetrate skin 92, muscle 93, and proximal cortex 95. Advancement of tissue penetrator 40 continues until collar 42 contacts proximal cortex 95 (MG. 17B). Thus, according to this embodiment, flange 32 acts as the depth control mechanism. Other depth control mechanisms may also be employed such as a probe, sensor, rib and any combination thereof. Once advancement is arrested, the end of tissue penetrator 40 is positioned in intraosseous space 96.

The reusable handle, which here includes housing 10 and spring 25, may be removed leaving tissue penetrator assembly 30 behind (FIG. 17C). Tissue penetrator assembly 30 includes hub 31 to provide stabilization of tissue penetrator 40 against the skin and to provide for additional security against accidental advancement or dislodgement during patient transport. Hub 31 incorporates a flange 32 at its distal end to provide for skin safety and better stabilization. After insertion of tissue penetrator 40 into the IO space hub 31 is adjusted by screw 33 or other mechanism so that it snuggly fits against the skin. Tissue penetrator 40 may be fixedly attached to screw 33 either before insertion or after insertion (e.g. by a locking mechanism). IO space 96 may then be aseptically accessed through connector 45.

Methods

One aspect of the invention is a method of establishing access to the intraosseous space including contacting the skin covering the manubrium of a subject with a device including a driver, a tissue penetrator, and a depth control mechanism, deploying the tissue penetrator. The term "subject" may include any vertebrate with a sternum. The term "operator" may include anyone who uses a device of the invention including, without limitation, a health care professional and the subject. The term "deploying the tissue penetrator" may mean advancing the tissue penetrator from its starting position a sufficient distance to situate the tip of the tissue penetrator in the IO space. The method may further include detaching the driver from the tissue penetrator after insertion of the tissue penetrator is achieved.

For example, according to the embodiments pictured in FIGS. 2-3, the operator inserts tissue penetrator 40 into the subject at the region shown in FIG. 1. Tissue penetrator 40, which includes a pressure sensor, detects the increase in pressure that occurs when the tip contacts anterior cortex 95. The sensor then activates driver 20 to advance tissue penetrator 40 until coupling end 24 (FIG. 2) or coupling end 26 (FIG. 3) contacts annular stop 50. While not expressly shown, a connector recessed in the coupling end may be used to access IO space 96. This access may optionally involve removal of portions of the device, such as housing 10, driver 20, driver shaft 23, and coupling end 24 or 26.

In a related embodiment shown in FIG. 5 tissue penetrator 40 includes a pressure-sensor (not expressly shown). Upon application of an axial force by the operator against the subject's sternum, tissue penetrator pierces the subjects skin, muscle, and subcutaneous tissue to contact bone. The sensor either directly or indirectly activates motor 22 to rotate tissue penetrator 40, thereby beginning drilling into the bone. Simultaneously or subsequently, gear 56 may engage ribs 55 to regulate the depth of drilling. For example, upon detecting a drop in pressure, the sensor may directly or indirectly brake or block further rotation of gear 56.

Although the present invention and its advantages have been described in detail, it should be understood that various changes, substitutions and alternations can be made herein without departing from the spirit and scope of the invention as defined by the following claims.

What is claimed is:

1. An apparatus for accessing bone marrow inside a bone, the apparatus comprising:
    a penetrator assembly comprising a tissue penetrator, the tissue penetrator configured to penetrate the bone and bone marrow, the tissue penetrator comprising a hollow cannula;
    a driver configured to insert a portion of the tissue penetrator into the bone and bone marrow;
    a housing having an end operable to contact a patient's skin during an insertion of the portion of the tissue penetrator into the bone and bone marrow; and
    a depth control mechanism configured to control the depth of penetration of the portion of the tissue penetrator into the bone and bone marrow, the depth control mechanism comprising a plurality of penetration shoulders disposed within the housing;
    wherein at least one of the plurality of penetration shoulders is configured to come into contact with another one of the plurality of penetration shoulders when advancing the tissue penetrator into the bone and bone marrow,
    wherein the portion of the tissue penetrator is disposed within the housing when the tissue penetrator is in an undeployed position, and
    wherein the portion of the tissue penetrator is disposed outside of the housing when the tissue penetrator is in a deployed position.

2. The apparatus of claim 1, wherein the depth control mechanism is configured to insert the tissue penetrator into the bone and bone marrow in two stages,
    wherein, in a first stage, the depth control mechanism controls the driver to insert the portion of the tissue penetrator through soft tissue proximate to the bone and bone marrow,
    wherein, in a second stage, the depth control mechanism controls the driver to insert the portion of the tissue penetrator through the bone and into the bone marrow.

3. The apparatus of claim 1, wherein each of the plurality of penetration shoulders comprises one or more of a pressure sensor and a trigger.

4. The apparatus of claim 3, wherein a first pressure sensor is configured to detect when a portion of the apparatus contacts a surface of the soft tissue proximate to the bone and bone marrow,
    wherein the depth control mechanism controls the driver to insert the portion of the tissue penetrator through soft tissue proximate to the bone and bone marrow in response to the first pressure sensor detecting that the portion of the tissue penetrator has contacted the surface of the soft tissue.

5. The apparatus of claim 4, wherein a second pressure sensor is configured to detect when the tissue penetrator contacts a surface of the bone,
    wherein the depth control mechanism controls the driver to insert the portion of the tissue penetrator through the bone and into the bone marrow in response to the second pressure sensor detecting that the tissue penetrator has contacted the surface of the bone.

6. The apparatus of claim 1, wherein the depth control mechanism further comprises a mechanical stop protruding from an inner surface of the housing, and wherein at least one of the plurality of penetration shoulders is configured to contact the mechanical stop when advancing the tissue penetrator into the bone and bone marrow.

7. An apparatus for accessing bone marrow inside a bone, the apparatus comprising:
    a housing;
    a penetrator assembly comprising a tissue penetrator, the tissue penetrator configured to penetrate the bone and bone marrow, the tissue penetrator comprising a hollow cannula;
    a driver disposed within the housing and configured to insert a portion of the tissue penetrator into the bone and bone marrow; and
    a depth control mechanism configured to control the depth of penetration of the tissue penetrator into the bone and bone marrow, the depth control mechanism comprising a mechanical stop formed on and protruding from an inner surface of the housing of the penetrator assembly.

8. The apparatus of claim 7, wherein the mechanical stop is an annular stop that traces an inner circumference of the housing.

9. The apparatus of claim 7, wherein the mechanical stop has a fixed position relative to the housing.

10. An apparatus for accessing bone marrow inside a bone of a patient, the apparatus comprising:
    a penetrator configured to penetrate a bone and bone marrow;
    a housing configured to contact a patient's skin during penetration of a portion of the penetrator into the bone and bone marrow;
    a driver including a drive shaft configured to drive the portion of the penetrator into the bone and bone marrow;
    a proximal penetration shoulder connected to the drive shaft;
    a distal penetration shoulder mounted on the penetrator; and
    a mechanical stop configured to stop advancement of the distal penetration shoulder during a first stage of insertion such that the portion of the penetrator contacts the bone, and
    wherein the proximal penetration shoulder is operable to advance a distance during a second stage of insertion such that the portion of the penetrator penetrates the bone and bone marrow.

11. The apparatus of claim 10, wherein the proximal penetration shoulder is connected to a threaded annulus.

12. The apparatus of claim 11, further comprising an intermediate penetration shoulder mounted on the threaded annulus.

13. The apparatus of claim 12, wherein the proximal and intermediate penetration shoulders are operable to advance toward the distal penetration shoulder during the first stage of insertion until the intermediate penetration shoulder contacts the distal penetration shoulder.

14. The apparatus of claim 13, wherein the proximal penetration shoulder is operable to advance toward the intermediate penetration shoulder during the second stage of insertion causing the portion of the penetrator to advance through the bone and into the bone marrow.

15. The apparatus of claim 10, wherein the mechanical stop protrudes from an inner surface of the housing.

16. The apparatus of claim 15, further comprising a second sensor configured to activate advancement of the penetrator during the second stage of insertion.

17. The apparatus of claim 15, wherein the proximal penetration shoulder and the distal penetration shoulder are disposed within the housing.

18. The apparatus of claim 10, further comprising a first sensor configured to activate advancement of the penetrator during the first stage of insertion.

* * * * *